US011339391B2

(12) United States Patent
Raymond et al.

(10) Patent No.: US 11,339,391 B2
(45) Date of Patent: May 24, 2022

(54) HIGH EFFICIENCY CONSTRUCTION OF DNA LIBRARIES

(71) Applicant: Resolution Bioscience, Inc., Kirkland, WA (US)

(72) Inventors: Christopher K. Raymond, Seattle, WA (US); Lee P. Lim, Kirkland, WA (US)

(73) Assignee: Resolution Bioscience, Inc., Kirkland, WA (US)

( * ) Notice: Subject to any disclaimer, the term of this patent is extended or adjusted under 35 U.S.C. 154(b) by 0 days.

(21) Appl. No.: 15/965,048

(22) Filed: Apr. 27, 2018

(65) Prior Publication Data

US 2018/0245072 A1  Aug. 30, 2018

Related U.S. Application Data

(63) Continuation of application No. PCT/US2016/061395, filed on Nov. 10, 2016.

(60) Provisional application No. 62/254,110, filed on Nov. 11, 2015.

(51) Int. Cl.
| C12N 15/10 | (2006.01) |
| C12Q 1/686 | (2018.01) |
| C12Q 1/6869 | (2018.01) |
| C12N 15/66 | (2006.01) |
| C12Q 1/6827 | (2018.01) |
| C12Q 1/6855 | (2018.01) |
| C12Q 1/6883 | (2018.01) |
| C12Q 1/6886 | (2018.01) |

(52) U.S. Cl.
CPC ......... *C12N 15/1093* (2013.01); *C12N 15/66* (2013.01); *C12Q 1/686* (2013.01); *C12Q 1/6827* (2013.01); *C12Q 1/6855* (2013.01); *C12Q 1/6869* (2013.01); *C12Q 1/6883* (2013.01); *C12Q 1/6886* (2013.01)

(58) Field of Classification Search
CPC .. C12N 15/1093; C12N 15/66; C12Q 1/6827; C12Q 1/6855; C12Q 1/686; C12Q 1/6869; C12Q 1/6883; C12Q 1/6886; C12Q 1/68; C12Q 2525/191
See application file for complete search history.

(56) References Cited

U.S. PATENT DOCUMENTS

| 5,591,582 A | 1/1997 | Bos et al. |
| 6,025,139 A | 2/2000 | Yager et al. |
| 6,480,791 B1 | 11/2002 | Strathmann |
| 6,812,341 B1 | 11/2004 | Conrad |
| 7,393,665 B2 | 7/2008 | Brenner |
| 8,148,068 B2 | 4/2012 | Brenner |
| 8,168,385 B2 | 5/2012 | Brenner |
| 8,318,433 B2 | 11/2012 | Brenner |
| 8,383,338 B2 | 2/2013 | Kitzman et al. |
| 8,470,996 B2 | 6/2013 | Brenner |
| 8,476,018 B2 | 7/2013 | Brenner |
| 8,828,688 B2 | 9/2014 | Namsaraev |
| 8,835,358 B2 | 9/2014 | Fodor et al. |
| 8,865,410 B2 | 10/2014 | Shendure et al. |
| 9,018,365 B2 | 4/2015 | Brenner |
| 9,085,798 B2 | 7/2015 | Chee |
| 9,121,069 B2 | 9/2015 | Lo et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,340,830 B2 | 5/2016 | Lipson et al. |
| 9,410,954 B2 | 8/2016 | Boshoff et al. |
| 9,546,399 B2 | 1/2017 | Amorese et al. |
| 9,598,731 B2 | 3/2017 | Talasaz |
| 9,702,002 B2 | 7/2017 | Boutell |
| 9,708,659 B2 | 7/2017 | Fodor et al. |
| 9,783,847 B2 | 10/2017 | Chee |
| 9,792,403 B2 | 10/2017 | Sun et al. |
| 9,816,137 B2 | 11/2017 | Fodor et al. |
| 9,834,822 B2 | 12/2017 | Talasaz |
| 9,840,743 B2 | 12/2017 | Talasaz |
| 9,850,523 B1 | 12/2017 | Chudova et al. |
| 9,902,992 B2 | 2/2018 | Talasaz et al. |
| 9,907,798 B2 | 3/2018 | Boshoff et al. |
| 9,920,366 B2 | 3/2018 | Eltoukhy et al. |
| 9,932,576 B2 | 4/2018 | Raymond et al. |
| 9,965,585 B2 | 5/2018 | Lo et al. |
| 10,000,800 B2 | 6/2018 | Chee |
| 10,047,394 B2 | 8/2018 | Fodor et al. |
| 10,059,991 B2 | 8/2018 | Fodor et al. |
| 10,095,831 B2 | 10/2018 | Duenwald et al. |
| 10,119,165 B2 | 11/2018 | Chee |
| 10,202,646 B2 | 2/2019 | Fodor et al. |
| 10,227,587 B2 | 3/2019 | Zhang et al. |
| 10,240,209 B2 | 3/2019 | Lo et al. |
| 10,266,883 B2 | 4/2019 | Chee |
| 10,266,889 B2 | 4/2019 | Behlke et al. |
| 10,287,630 B2 | 5/2019 | Xie et al. |
| 10,297,342 B2 | 5/2019 | Lo et al. |
| 10,378,064 B1 | 8/2019 | Schutz et al. |
| 10,388,403 B2 | 8/2019 | Rava et al. |
| 10,392,661 B2 | 8/2019 | Fodor et al. |
| 10,453,556 B2 | 10/2019 | Lo et al. |
| 10,494,678 B2 | 12/2019 | Talasaz |
| 10,501,793 B2 | 12/2019 | Chee |
| 10,501,810 B2 | 12/2019 | Talasaz |

(Continued)

FOREIGN PATENT DOCUMENTS

| CN | 101932729 A | 12/2010 |
| CN | 102439177 A | 5/2012 |

(Continued)

OTHER PUBLICATIONS

Extended European Search Report in Application No. EP 16865029.9, dated Apr. 29, 2019, 11 pages.

(Continued)

*Primary Examiner* — Robert H Havlin
(74) *Attorney, Agent, or Firm* — Cooley LLP

(57) ABSTRACT

The invention provides a method for efficient DNA library construction and targeted genetic analyses of the libraries.

23 Claims, 5 Drawing Sheets

Specification includes a Sequence Listing.

(56) References Cited

U.S. PATENT DOCUMENTS

| | | | |
|---|---|---|---|
| 10,538,759 B2 | 1/2020 | Stuelpnagel et al. |
| 10,577,601 B2 | 3/2020 | Shendure et al. |
| 10,597,653 B2 | 3/2020 | Sabot et al. |
| 10,597,708 B2 | 3/2020 | Zimmermann et al. |
| 10,597,709 B2 | 3/2020 | Zimmermann et al. |
| 10,619,203 B2 | 4/2020 | Fodor et al. |
| 10,619,214 B2 | 4/2020 | Lo et al. |
| 10,689,699 B2 | 6/2020 | Salk et al. |
| 10,704,085 B2 | 7/2020 | Talasaz et al. |
| 10,704,086 B2 | 7/2020 | Talasaz et al. |
| 10,741,270 B2 | 8/2020 | Lo et al. |
| 10,752,951 B2 | 8/2020 | Salk et al. |
| 10,793,916 B2 | 10/2020 | Talasaz |
| 10,801,063 B2 | 10/2020 | Eltoukhy et al. |
| 10,847,249 B2 | 11/2020 | Sun et al. |
| 10,876,152 B2 | 12/2020 | Talasaz et al. |
| 10,883,139 B2 | 1/2021 | Eltoukhy et al. |
| 10,889,858 B2 | 1/2021 | Talasaz et al. |
| 10,894,974 B2 | 1/2021 | Talasaz et al. |
| 10,907,149 B2 | 2/2021 | Raymond et al. |
| 2003/0148310 A1 | 8/2003 | Sorge |
| 2004/0058328 A1 | 3/2004 | Chan et al. |
| 2005/0032057 A1 | 2/2005 | Shoemaker et al. |
| 2007/0037139 A1 | 2/2007 | Tomono et al. |
| 2007/0128624 A1 | 6/2007 | Gormley et al. |
| 2007/0172873 A1 | 7/2007 | Brenner et al. |
| 2008/0038782 A1 | 2/2008 | Borns |
| 2009/0117573 A1 | 5/2009 | Fu et al. |
| 2009/0143243 A1 | 6/2009 | Gunning et al. |
| 2009/0191563 A1 | 7/2009 | Steemers et al. |
| 2009/0264305 A1 | 10/2009 | Brandon et al. |
| 2010/0093550 A1 | 4/2010 | Stuelpnagel et al. |
| 2010/0273219 A1 | 10/2010 | May et al. |
| 2011/0014657 A1 | 1/2011 | Rigatti et al. |
| 2011/0160078 A1 | 6/2011 | Fodor et al. |
| 2011/0294689 A1 | 12/2011 | Namsaraev |
| 2011/0313145 A1 | 12/2011 | Sharon et al. |
| 2012/0157322 A1 | 6/2012 | Myllykangas et al. |
| 2013/0288915 A1 | 10/2013 | Seligmann et al. |
| 2014/0100792 A1 | 4/2014 | Deciu et al. |
| 2014/0242581 A1 | 8/2014 | Johnson |
| 2014/0274731 A1 | 9/2014 | Raymond et al. |
| 2014/0274740 A1 | 9/2014 | Srinivasan et al. |
| 2015/0046180 A1 | 2/2015 | Futscher De Deus et al. |
| 2015/0072344 A1 | 3/2015 | Wiley |
| 2015/0111757 A1 | 4/2015 | Boyden et al. |
| 2015/0159222 A1 | 6/2015 | Gaulis et al. |
| 2015/0275289 A1 | 10/2015 | Otwinowski et al. |
| 2015/0376700 A1 | 12/2015 | Schnall-Levin et al. |
| 2016/0053253 A1 | 2/2016 | Salathia et al. |
| 2016/0053301 A1 | 2/2016 | Raymond et al. |
| 2017/0088887 A1 | 3/2017 | Makarov et al. |
| 2017/0096706 A1 | 4/2017 | Behlke et al. |
| 2017/0242960 A1 | 8/2017 | Rabinowitz et al. |
| 2017/0283869 A1* | 10/2017 | Fang ............... C12P 19/34 |
| 2017/0355984 A1 | 12/2017 | Evans et al. |
| 2017/0356053 A1 | 12/2017 | Otto et al. |
| 2018/0142234 A1 | 5/2018 | Raymond et al. |
| 2018/0163272 A1 | 6/2018 | Raymond et al. |
| 2018/0179578 A1 | 6/2018 | Raymond et al. |
| 2018/0300449 A1 | 10/2018 | Kermani et al. |
| 2018/0300456 A1 | 10/2018 | Eltoukhy et al. |
| 2018/0363066 A1 | 12/2018 | Chalmers et al. |
| 2019/0032112 A1 | 1/2019 | Lipson et al. |
| 2019/0136301 A1 | 5/2019 | Lipson et al. |
| 2019/0233897 A1 | 8/2019 | Cronin et al. |
| 2020/0048703 A1 | 2/2020 | Chee |
| 2020/0299775 A1 | 9/2020 | Hawryluk et al. |
| 2021/0198658 A1 | 7/2021 | Raymond et al. |

FOREIGN PATENT DOCUMENTS

| | | |
|---|---|---|
| CN | 103103624 A | 5/2013 |
| CN | 103668471 A | 3/2014 |
| EP | 3192869 A1 | 7/2017 |
| EP | 3202915 A1 | 8/2017 |
| EP | 3 363 904 A2 | 8/2018 |
| EP | 3421613 A1 | 1/2019 |
| EP | 3470533 A1 | 4/2019 |
| EP | 3502273 A1 | 6/2019 |
| EP | 3551769 A1 | 10/2019 |
| EP | 3567120 A1 | 11/2019 |
| JP | 2013-536679 A | 9/2013 |
| JP | 2014-512817 | 5/2014 |
| JP | 2020516281 A | 6/2020 |
| WO | WO 1999/011819 A1 | 3/1999 |
| WO | WO 2004/053127 A1 | 6/2004 |
| WO | WO 2009/076238 A2 | 6/2009 |
| WO | WO 2009/091798 A1 | 7/2009 |
| WO | WO 2010/129937 A2 | 11/2010 |
| WO | WO 2011/156529 A2 | 12/2011 |
| WO | WO 2012/028746 A1 | 3/2012 |
| WO | WO 2012/040387 A1 | 3/2012 |
| WO | WO 2012/129363 A2 | 9/2012 |
| WO | WO 2012/142213 A2 | 10/2012 |
| WO | WO 2012/142334 A1 | 10/2012 |
| WO | WO 2012/148477 A1 | 11/2012 |
| WO | WO 2014/052487 A1 | 4/2014 |
| WO | WO 2014/055790 A2 | 4/2014 |
| WO | WO 2014/071295 A1 | 5/2014 |
| WO | WO 2014/093330 A1 | 6/2014 |
| WO | WO 2014/093825 A1 | 6/2014 |
| WO | WO 2014/122288 A1 | 8/2014 |
| WO | WO 2015/134552 A1 | 9/2014 |
| WO | WO 2015/117040 A1 | 8/2015 |
| WO | WO 2015/134552 A1 | 9/2015 |
| WO | WO 2016/022833 A1 | 2/2016 |
| WO | WO 2016/028316 A1 | 2/2016 |
| WO | WO 2016/037389 A1 | 3/2016 |
| WO | WO 2016/040901 A1 | 3/2016 |
| WO | WO 2016/094853 A1 | 6/2016 |
| WO | WO 2016/109452 A1 | 7/2016 |
| WO | WO 2017/083562 A1 | 5/2017 |
| WO | WO 2018/039463 A1 | 3/2018 |
| WO | WO 2018/064629 A1 | 4/2018 |
| WO | WO 2018/094183 A1 | 5/2018 |
| WO | WO-2018104908 A2 | 6/2018 |
| WO | WO-2020106906 A1 | 5/2020 |

OTHER PUBLICATIONS

"How many species of bacteria are there?" WiseGeek.com, accessed Jan. 21, 2014, 2 pages. (Year: 2014).

"List of sequenced bacterial genomes" Wikipedia.com, accessed Jan. 24, 2014, 57 pages. (Year: 2014).

Atamaniuk et al., "Cell-free plasma DNA: a marker for apoptosis during hemodialysis." Clinical Chemistry (2006); 52.3: 523-526.

Blake, R. D., and Delcourt, S.G. "Thermodynamic effects of formamide on DNA stability." Nucleic Acids Research (1996); 24.11: 2095-2103.

Chan et al. "Cancer genome scanning in plasma: detection of tumor-associated copy number aberrations, single-nucleotide variants, and tumoral heterogeneity by massively parallel sequencing." Clinical Chemistry (2013); 59(1): 211-224.

Extended European Search Report in Application No. EP 13862440.8, dated Oct. 11, 2016, 19 pages.

Hoeijmakers et al., "Linear amplification for deep sequencing." Nature Protocols (2011); 6.7: 1026-1036.

KAPA Biosystems, "KAPA Library Quantification Kits Technical Data Sheet" (2011); 6 pages, www.kapabiosystems.com.

Leary et al. "Detection of chromosomal alterations in the circulation of cancer patients with whole-genome sequencing." Science Translational Medicine (2012); 4(162):162ra154.

Lin et al., "Exon array profiling detects EML4-ALK fusion in breast, colorectal, and non-small cell lung cancers." Molecular Cancer Research (2009); 7.9:1466-1476.

Mano, H., "Non-solid oncogenes in solid tumors: EML4-ALK fusion genes in lung cancer." Cancer Science (2008); 99.12: 2349-2355.

(56) References Cited

OTHER PUBLICATIONS

McKernan et al., "Sequence and structural variation in a human genome uncovered by short-read, massively parallel ligation sequencing using two-base encoding." Genome Research (2009); 19.9: 1527-1541.
Melchior, W.B. and Hippel, P.H. "Alteration of the relative stability of dA• dT and dG• dC base pairs in DNA." Proceedings of the National Academy of Sciences USA (1973); 70.2: 298-302.
Meyer et al., "Targeted high-throughput sequencing of tagged nucleic acid samples." Nucleic Acids Research (2007); 35.15: e97, 5 pages.
Meyer et al., "From micrograms to picograms: quantitative PCR reduces the material demands of high-throughput sequencing" Nucleic Acids Research (2008); 36(1 ):e5.
Partial Supplementary European Search Report in European Application No. 13862440.8 dated Jul. 4, 2016, 11 pages.
PCT/US2013/074102, International Preliminary Report on Patentability dated Jun. 16, 2015.
PCT/US2014/052317, International Preliminary Report on Patentability dated Feb. 28, 2017, 8 pages.
PCT/US2013/074102, International Search Report and Written Opinion dated Feb. 28, 2014.
PCT/US2014/052317, International Search Report and Written Opinion dated Jan. 13, 2015, 13 pages.
PCT/US2016/061395, International Preliminary Report on Patentability dated May 15, 2018, 10 pages.
PCT/US2016/061395, International Search Report and Written Opinion dated Feb. 7, 2017, 14 pages.
PCT/US2017/048434, International Search Report and Written Opinion dated Dec. 26, 2017, 15 pages.
Samorodnitsky, et al., "Comparison of Custom Capture for Targeted Next-Generation DNA Sequencing." The Journal of Molecular Diagnostics (2015); 17(1): 64-75.
Shevelev and Hübscher, "The 3' 5' exonucleases", *Nat Rev Mol Cell Biol.*, 3(5): 364-376 (2002).
Shiroguchi, et al., "Digital RNA sequencing minimizes sequence-dependent bias and amplification noise with optimized single-molecule barcodes." PNAS (2012); 109(4): 1347-1352, Supporting Information, 14 pages.
Stellwagen, Earle, et al., "Monovalent cation size and DNA conformational stability." Biochemistry (2011); 50.15: 3084-3094.
Taton, T. Andrew, et al., "Scanometric DNA array detection with nanoparticle probes." Science (2000); 289.5485: 1757-1760.
Vogelstein et al., "Cancer genome landscapes." Science (2013); 339.6127: 1546-1558.
Yegnasubramanian et al., "Preparation of Fragment Libraries for Next-Generation Sequencing on the Applied Biosystems SOLiD Platform." Methods in Enzymology (2013); 529: 185-200.
Extended European Search Report in Application No. EP 19153893.3, dated Sep. 17, 2019, 9 pages.
Extended European Search Report in Application No. EP 21152311.3, dated Sep. 7, 2021, 14 pages.
[Author Unknown] "SureSelect$^{XT}$ Target Enrichment System for Illumina Paired-End Multiplexed Sequencing Library". Protocol, Version C3, Sep. 2019, Agilent Technologies, © Agilent Technologies, Inc. 2010-2019, 100 pages.
Begley, Sharon, "Psst, The Human Genome Was Never Completely Sequenced. Some Scientists Say It Should Be", STAT News, Jun. 20, 2017 (Year: 2017), downloaded Sep. 3, 2018 from https://www.statnews.com/2017 /06/20/human-genome-not-fully-sequenced/, 8 pages.
Cheng, et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology". J Mol Diagn. (May 2015); 17(3): 251-264. Epub Mar. 20, 2015.

Extended European Search Report in Application No. EP 17844424.6, dated Mar. 27, 2020, 8 pages.
Fakruddin, et al., "Nucleic acid amplification: Alternative methods of polymerase chain reaction". Journal of Pharmacy and Bioallied Sciences (Oct.-Dec. 2013); 5(4): 245-252.
Forster, et al., "A human gut bacterial genome and culture collection for improved metagenomic analyses". Nat Biotechnol. (Feb. 2019); 37(2): 186-192. Epub Feb. 4, 2019.
Horn, Susanne, "Target Enrichment via DNA Hybridization Capture" in Ancient DNA: Methods and Protocols, Methods in Molecular Biology (2012); 840: 177-188. Epub Dec. 8, 2011.
Jacobs, et al., "The thermal stability of oligonucleotide duplexes is sequence independent in tetraalkylammonium salt solutions: application to identifying recombinant DNA clones". Nucleic Acids Res. (May 25, 1988); 16(10): 4637-4650.
PCT/US2017/048434, International Preliminary Report on Patentability dated Feb. 26, 2019, 10 pages.
Piovesan, et al., "On the length, weight and GC content of the human genome". BMC Res Notes (Feb. 27, 2019); 12: 106, 7 pages.
Rittié and Perbal, "Enzymes used in molecular biology: a useful guide". J. Cell Commun. Signal. (Jun. 2008); 2 (1-2): 25-45. Epub Sep. 3, 2008.
Shevelev and Hübscher, "The 3' 5' exonucleases", Nat Rev Mol Cell Biol. (May 2002); 3(5): 364-376.
Oxford Dictionary of Biochemistry and Molecular Biology, Definition of "base composition", general eds Attwood, et al. Revised Edition (2000), 3 pages.
Beltran, et al., "Circulating tumor DNA profile recognizes transformation to castration-resistant neuroendocrine prostate cancer". J Clin Invest (Apr. 1, 2020); 130(4): 1653-1668.
Miura, et al., "Highly efficient single-stranded DNA ligation technique improves low-input whole-genome bisulfite sequencing by post-bisulfite adaptor tagging." Nucleic Acids Research (Sep. 5, 2019); 47(15): e85-e85, p. 1-10.
Zhou, et al., "Systematic evaluation of library preparation methods and sequencing platforms for high-throughput whole genome bisulfite sequencing." Scientific Reports (2019); 9: 10383, 16 pages.
[Author Unknown] "TruSeq™ RNA and DNA Library Preparation Kits v2" . Data Sheet: Illumnia® Sequencing, © 2011, 2014, Illumina, Inc., Pub. No. 770-2009-039 Current as of Nov. 17, 2014, 4 pages.
Hess, et al., "Library preparation for next generation sequencing: A review of automation strategies". Biotechnol Adv. (Jul.-Aug. 2020); 41: 107537, 14 pages. Epub Mar. 19, 2020.
Hong and Shin, "Bisulfite-Converted DNA Quantity Evaluation: A Multiplex Quantitative Real-Time PCR System for Evaluation of Bisulfite Conversion". Front Genet. (Feb. 25, 2021); 12: 618955. eCollection 2021.
Ma, et al., "Pan-cancer genome and transcriptome analyses of 1,699 paediatric leukaemias and solid tumours". Nature (2018); 55: 371-376. Epub Feb. 28, 2018.
Malone, et al., "Molecular profiling for precision cancer therapies". Genome Med. (Jan. 14, 2020); 12(1): 8, 19 pages.
Mamanova, et al., "Target-enrichment strategies for next-generation sequencing". Nature Methods. (Feb. 2010); 7(2): 111-118.
Manier, et al., "Whole-exome sequencing of cell-free DNA and circulating tumor cells in multiple myeloma". Nat Commun. (Apr. 27, 2018); 9(1): 1691, 11 pages.
PCT/US2021/049448, International Search Report and Written Opinion dated Dec. 28, 2021, 12 pages.
Wang, et al., "Enzymatic approaches for profiling cytosine methylation and hydroxymethylation". Mol Metab. (Mar. 2022); 57: 101314. Epub Aug. 8, 2021.
Wang, et al., "Low-pass genome sequencing versus chromosomal microarray analysis: implementation in prenatal diagnosis". Genet Med. (Mar. 2020); 22(3): 500-510. Epub Aug. 26, 2019.

* cited by examiner

*Conventional Ligation*

*High Efficiency (HE) Ligation*

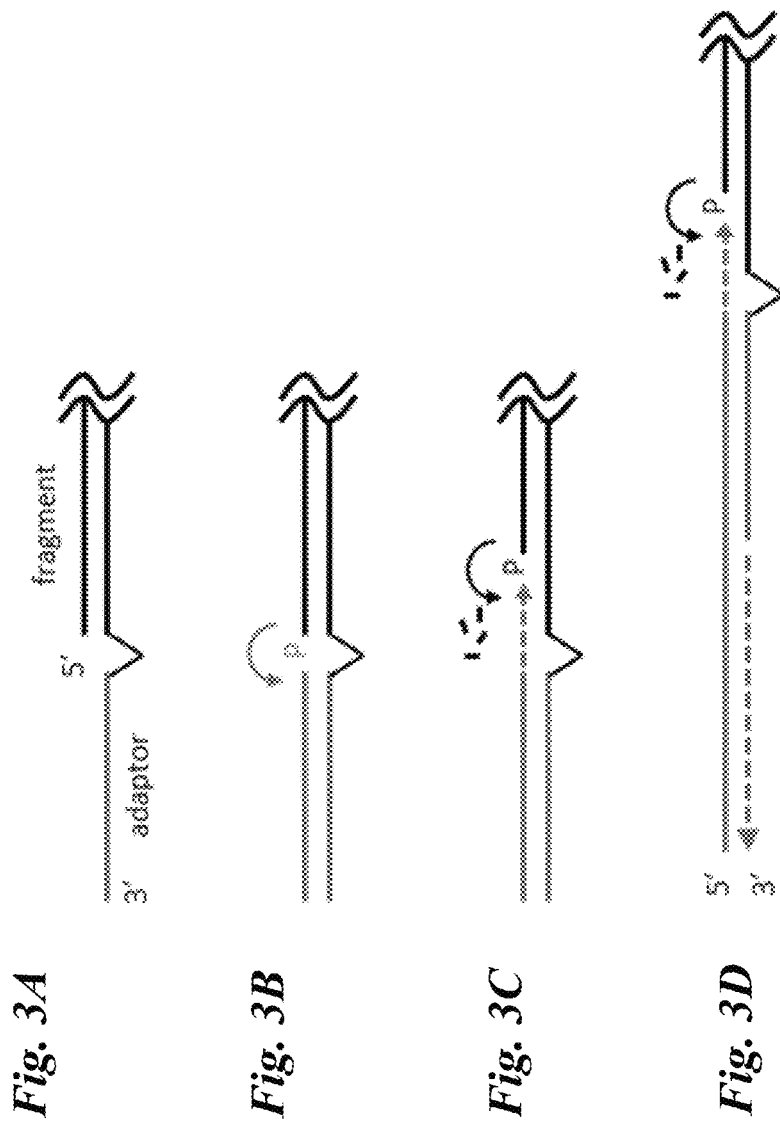

HIGH EFFICIENCY CONSTRUCTION OF DNA LIBRARIES

CROSS-REFERENCE TO RELATED APPLICATIONS

This application is a continuation of International Patent Application No. PCT/US2016/061395, filed Nov. 10, 2016, which claims the benefit of priority to U.S. Provisional Application No. 62/254,110, filed Nov. 11, 2015, the contents of which are hereby incorporated by reference in their entireties.

REFERENCE TO THE ELECTRONIC TEXT FILE SUBMITTED HEREWITH

The contents of the text file submitted electronically herewith are incorporated herein by reference in their entirety: A computer readable format copy of the Sequence Listing (filename: CLFK_003_01US SeqList_ST25.txt, date recorded: Apr. 24, 2018, file size: 17.7 kilobytes).

BACKGROUND

Technical Field

The invention relates generally to improved compositions and methods for constructing DNA libraries. In particular, the present invention relates to efficiently constructing DNA clone libraries for quantitative genetic analyses.

Description of the Related Art

Various DNA specimens that are of interest for downstream analysis are collected in minute quantities. By way of example, cell-free DNA (cfDNA) collected from the plasma fraction of whole blood is generally present in nanogram quantities per mL of plasma. Given that one diploid human genome weighs 6 picograms, this means there are a few hundred to a few thousand total genomes of information that can be isolated from a single blood draw.

In cancer patients, tumor DNA is shed into the bloodstream in highly variable quantities ranging from ≤0.1% to ≥10% total circulating DNA. Blood draws contain only a few nanograms of DNA and if tumor genomes are present at 0.1% of the total circulating DNA, then only 1 to 10 total copies of the tumor genome are present. To unambiguously identify tumor DNA by sequence analysis, it is necessary to observe two or more copies of a tumor-specific genetic lesion. However, the need to maximize the detection sensitivity of DNA, meaning accurate detection of tumor DNA in the 0.1% range has yet to be achieved These considerations illuminate the fundamental problem that reliable genetic analysis of solid tumors using blood is governed, in part, by the ability isolate and analyze rare genomic fragments. Moreover, many therapeutically actionable tumor lesions involve gene fusions, significant insertions or deletions of DNA sequence and/or changes in gene copy number. Such alterations are refractory to analysis by PCR, where two adjacent primer binding sites must be known and where copy variation is obscured by many rounds of target amplification.

At present, target retrieval methods are used for comprehensive analysis of potential lesions in circulating tumor DNA. Such retrieval methods rely on the creation of DNA clone libraries. Unfortunately, current methods for creating these DNA libraries are inefficient, with only a small percentage of DNA fragments being successfully converted to useful library clones.

BRIEF SUMMARY

The invention relates generally to compositions and methods for high efficiency attachment of DNA adaptors to DNA fragments to generate DNA libraries for quantitative genetic analyses.

In various embodiments, a method for increasing the efficiency of adaptor ligation to one or more DNA fragments comprising: removing the terminal phosphate residues of one or more DNA fragments; treating the dephosphorylated DNA fragments with one or more end-repair enzymes to generate end-repaired DNA; ligating one or more double-stranded DNA (dsDNA) pre-adaptors to the 3' end of each strand of the end-repaired DNA to form pre-adaptor/end-repaired DNA complexes, wherein each dsDNA pre-adaptor comprises a ligation strand oligonucleotide that is ligated to the 3' end of each strand of the end-repaired DNA, and a non-ligation partner strand oligonucleotide; displacing the non-ligation partner strand oligonucleotide from the pre-adaptor/end-repaired DNA complexes with a repair oligonucleotide, to form adaptor/end-repaired DNA complexes, wherein each adaptor comprises the ligation strand oligonucleotide and the repair oligonucleotide; and treating the adaptor/end-repaired DNA complexes with one or more enzymes to form a contiguous, double-stranded, DNA library; wherein the efficiency of adapter ligation is increased compared to a method wherein dephosphorylated adapter molecules are ligated to phosphorylated DNA fragments is provided.

In various embodiments, a method for constructing a DNA library comprising: removing the terminal phosphate residues of one or more DNA fragments; treating the dephosphorylated DNA fragments with one or more end-repair enzymes to generate end-repaired DNA; ligating one or more double-stranded DNA (dsDNA) pre-adaptors to the 3' end of each strand of the end-repaired DNA to form pre-adaptor/end-repaired DNA complexes, wherein each dsDNA pre-adaptor comprises a ligation strand oligonucleotide that is ligated to the 3' end of each strand of the end-repaired DNA, and a non-ligation partner strand oligonucleotide; displacing the non-ligation partner strand oligonucleotide from the pre-adaptor/end-repaired DNA complexes with a repair oligonucleotide, to form adaptor/end-repaired DNA complexes, wherein each adaptor comprises the ligation strand oligonucleotide and the repair oligonucleotide; and treating the adaptor/end-repaired DNA complexes with one or more enzymes to form a contiguous, double-stranded, DNA library is provided.

In particular embodiments, the non-ligation partner strand oligonucleotide comprises a modification at the 3' terminus that prevents its ligation to the 5' end of the end-repaired DNA and/or adaptor dimer formation.

In certain embodiments, the source of the one or more DNA fragments is DNA selected from the group consisting of: genomic DNA (gDNA), complementary DNA (cDNA), and cell-free DNA (cfDNA).

In further embodiments, the source of the DNA is a biological sample selected from the group consisting of: blood, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy sample.

In particular embodiments, the source of the DNA is a biological sample selected from the group consisting of: amniotic fluid, blood, plasma, serum, semen, lymphatic fluid, cerebral spinal fluid, ocular fluid, urine, saliva, stool, mucous, and sweat.

In further embodiments, the methods further comprise isolating the DNA from a biological sample of a subject.

In some embodiments, the methods further comprise fragmenting the DNA from a biological sample of a subject.

In certain embodiments, the methods further comprise repairing damage of the one or more DNA fragments prior to ligation.

In particular embodiments, the damage is a deaminated cytosine (Uracil), an abasic site, methylation of guanine to O6MeG, DNA nicks, gaps, or a thymine dimer.

In various embodiments, a method constructing a cfDNA library comprising: isolating or obtaining cfDNA from a biological sample of a subject; removing the terminal phosphate residues of the cfDNA; treating the dephosphorylated cfDNA with one or more end-repair enzymes to generate end-repaired cfDNA, and optionally to repair DNA damage; ligating one or more double-stranded DNA (dsDNA) pre-adaptors to the 3' end of each strand of the end-repaired cfDNA to form pre-adaptor/end-repaired cfDNA complexes, wherein each dsDNA pre-adaptor comprises a ligation strand oligonucleotide that is ligated to the 3' end of each strand of the end-repaired cfDNA, and a non-ligation partner strand oligonucleotide; displacing the non-ligation partner strand oligonucleotide from the pre-adaptor/end-repaired cfDNA complexes with a repair oligonucleotide, to form adaptor/end-repaired cfDNA complexes, wherein each adaptor comprises the ligation strand oligonucleotide and the repair oligonucleotide; treating the adaptor/end-repaired cfDNA complexes with one or more enzymes to form a contiguous, double-stranded, cfDNA library; and amplifying the cfDNA library to generate a cell-free DNA clone library is provided.

In particular embodiments, the ligation strand oligonucleotide comprises one or more modifications to prevent adaptor dimer formation, optionally wherein the modification of the 3' end of the no-ligation partner strand oligonucleotide prevents adaptor dimer formation.

In certain embodiments, the ligation strand oligonucleotide comprises an anchor sequence, a read code, or a PCR primer binding site.

In further embodiments, the ligation strand oligonucleotide comprises an anchor sequence, a read code, and a PCR primer binding site.

In some embodiments, the ligation strand oligonucleotide comprises one or more PCR primer binding sites for PCR amplification of the one or more contiguous, double-stranded, DNA library molecules.

In particular embodiments, the ligation strand oligonucleotide comprises one or more unique read codes.

In particular embodiments, the ligation strand oligonucleotide comprises one or more sample codes for sample multiplexing.

In certain embodiments, the ligation strand oligonucleotide comprises one or more sequences for DNA sequencing.

In further embodiments, the ligation strand oligonucleotide comprises an anchor sequence.

In further embodiments, the repair oligonucleotide comprises an anchor sequence, a read code, or a PCR primer binding site.

In certain embodiments, the repair oligonucleotide comprises an anchor sequence, a read code, and a PCR primer binding site.

In particular embodiments, the repair oligonucleotide comprises one or more primer binding sites for PCR amplification of the one or more contiguous, double-stranded, DNA library molecules.

In some embodiments, the repair oligonucleotide comprises one or more unique read codes.

In certain embodiments, the repair oligonucleotide comprises one or more sample codes for sample multiplexing.

In particular embodiments, the repair oligonucleotide comprises one or more sequences for DNA sequencing.

In further embodiments, the ligation strand oligonucleotide is complementary to the repair oligonucleotide.

In particular embodiments, the anchor sequence of the ligation strand oligonucleotide is complementary to the anchor sequence of the repair oligonucleotide.

In further embodiments, the PCR primer binding site of the ligation strand oligonucleotide is complementary to the PCR primer binding site of the repair oligonucleotide.

In particular embodiments, the one or more adaptors comprises a plurality of ligation strand oligonucleotide species.

In some embodiments, the one or more adaptors comprises a plurality of repair oligonucleotide species.

In particular embodiments, the primer binding site of the ligation strand oligonucleotide is not complementary to the primer binding site of the repair oligonucleotide.

In certain embodiments, the primer binding site of the ligation strand oligonucleotide is substantially different from the primer binding site of the repair oligonucleotide.

In certain embodiments, a primer that binds the primer binding site of the ligation strand oligonucleotide does not substantially bind the primer binding site of the repair oligonucleotide.

In particular embodiments, the DNA library is amplified to generate a DNA clone library.

In further embodiments, qPCR is performed on the DNA clone library and a qPCR measurement is compared to standards of known genome equivalents to determine the genome equivalents of the DNA clone library.

In particular embodiments, the qPCR is performed with a primer that binds to an Alu sequence and a primer that binds to a sequence in an adaptor.

In some embodiments, quantitative genetic analysis is performed on a plurality of genetic loci in the DNA clone library.

In particular embodiments, quantitative genetic analysis is performed on a plurality of genetic loci in a plurality of DNA clone libraries.

In particular embodiments, quantitative genetic analysis comprises hybridizing one or more capture probes to a target genetic locus to form capture probe module-DNA clone complexes.

In certain embodiments, quantitative genetic analysis comprises isolating the capture probe-DNA clone complexes.

In further embodiments, the quantitative genetic analysis comprises amplification of the DNA clone sequence in the isolated capture probe-DNA clone complexes.

In particular embodiments, quantitative genetic analysis comprises DNA sequencing to generate a plurality of sequencing reads.

In further embodiments, the methods further comprise bioinformatic analysis of the plurality of sequencing reads.

In particular embodiments, quantitative genetic analysis is performed on a plurality of genetic loci in the DNA clone library and wherein bioinformatic analysis is used: to quantify the number of genome equivalents analyzed in the DNA clone library; to detect genetic variants in a target genetic locus; to detect mutations within a target genetic locus; to detect genetic fusions within a target genetic locus; and/or to measure copy number fluctuations within a target genetic locus.

In certain embodiments, the quantitative genetic analysis is used to identify or detect one or more genetic lesions that cause or associated with the genetic disease.

In particular embodiments, the genetic lesion comprises a nucleotide transition or transversion, a nucleotide insertion or deletion, a genomic rearrangement, a change in copy number, or a gene fusion.

In certain embodiments, the genetic disease is cancer.

In further embodiments, the quantitative genetic analysis is used to identify or detect one or more genetic variants or genetic lesions of one or more target genetic loci in fetal cfDNA.

In some embodiments, the capture probe is a component of a capture probe module that is optionally duplexed with a hapten-labeled partner oligonucleotide that hybridizes to a tail sequence in the capture probe module.

In various embodiments, a method of predicting, diagnosing, or monitoring a genetic disease in a subject comprising: isolating or obtaining DNA from a biological sample of a subject; removing the terminal phosphate residues of the DNA; treating the dephosphorylated DNA with one or more end-repair enzymes to generate end-repaired DNA; ligating one or more double-stranded DNA (dsDNA) pre-adaptors to the 3' end of each strand of the end-repaired DNA to form pre-adaptor/end-repaired DNA complexes, wherein each dsDNA pre-adaptor comprises a ligation strand oligonucleotide that is ligated to the 3' end of each strand of the end-repaired DNA, and a non-ligation partner strand oligonucleotide; displacing the non-ligation partner strand oligonucleotide from the pre-adaptor/end-repaired DNA complexes with a repair oligonucleotide, to form adaptor/end-repaired DNA complexes, wherein each adaptor comprises the ligation strand oligonucleotide and the repair oligonucleotide; treating the adaptor/end-repaired DNA complexes with one or more enzymes to form a contiguous, double-stranded, DNA library; amplifying the DNA library to generate a DNA clone library; determining the number of genome equivalents in the DNA clone library; and performing a quantitative genetic analysis of one or more target genetic loci associated with the genetic disease in the DNA clone library, wherein the identification or detection of one or more genetic lesions in the one or more target genetic loci is prognostic for, diagnostic of, or monitors the progression of the genetic disease is provided.

In certain embodiments, the DNA is genomic DNA, DNA from formalin-fixed, paraffin embedded (FFPE) samples, cDNA, or cfDNA.

In particular embodiments, the cfDNA is isolated from a biological sample selected from the group of: amniotic fluid, blood, plasma, serum, semen, lymphatic fluid, cerebral spinal fluid, ocular fluid, urine, saliva, stool, mucous, and sweat.

In further embodiments, the genetic lesion comprises a nucleotide transition or transversion, a nucleotide insertion or deletion, a genomic rearrangement, a change in copy number, or a gene fusion.

In particular embodiments, the genetic disease is cancer.

In various embodiments, a companion diagnostic for a genetic disease comprising: isolating or obtaining DNA from a biological sample of a subject; removing the terminal phosphate residues of the DNA; treating the dephosphorylated DNA with one or more end-repair enzymes to generate end-repaired DNA; ligating one or more double-stranded DNA (dsDNA) pre-adaptors to the 3' end of each strand of the end-repaired DNA to form pre-adaptor/end-repaired DNA complexes, wherein each dsDNA pre-adaptor comprises a ligation strand oligonucleotide that is ligated to the 3' end of each strand of the end-repaired DNA, and a non-ligation partner strand oligonucleotide; displacing the non-ligation partner strand oligonucleotide from the pre-adaptor/end-repaired DNA complexes with a repair oligonucleotide, to form adaptor/end-repaired DNA complexes, wherein each adaptor comprises the ligation strand oligonucleotide and the repair oligonucleotide; treating the adaptor/end-repaired DNA complexes with one or more enzymes to form a contiguous, double-stranded, DNA library; amplifying the DNA library to generate a DNA clone library; determining the number of genome equivalents in the DNA clone library; and performing a quantitative genetic analysis of one or more biomarkers associated with the genetic disease in the DNA clone library, wherein detection of, or failure to detect, at least one of the one or more biomarkers indicates whether the subject should be treated for the genetic disease is provided.

In further embodiments, the DNA is genomic DNA, DNA from formalin-fixed, paraffin embedded (FFPE) samples, cDNA, or cfDNA.

In particular embodiments, the cfDNA is isolated from a biological sample selected from the group consisting of: amniotic fluid, blood, plasma, serum, semen, lymphatic fluid, cerebral spinal fluid, ocular fluid, urine, saliva, stool, mucous, and sweat.

In particular embodiments, the biomarker is a genetic lesion.

In further embodiments, the genetic lesion comprises a nucleotide transition or transversion, a nucleotide insertion or deletion, a genomic rearrangement, a change in copy number, or a gene fusion.

In certain embodiments, the genetic disease is cancer.

BRIEF DESCRIPTION OF THE SEVERAL VIEWS OF THE DRAWINGS

(FIG. 1A) Target DNA fragments are 5' phosphorylated prior to DNA ligation with unphosphorylated duplex adapters. (FIG. 1B) A common inefficiency with conventional ligation approaches is that 5' target DNA fragment ends lacking a phosphate group fails to ligate with unphosphorylated duplex adapters. (FIG. 1C) Ligation of target DNA fragments to one another. (FIG. 1D) Duplex adaptor comprising a 5' phosphate group required is ligated to 3' end of target DNA fragment The hatched circle one the partner strand oligonucleotide of the adaptor represents a 3' blocking group. (FIG. 1E) The 3' blocking group also prevents adaptors from ligating to one another. (FIG. 1F) Occasional adaptor duplexes lacking a 5' phosphate fail to ligate to target fragments.

FIG. 3A-FIG. 3D show exemplary methods of completing HE ligated constructs. (FIG. 3A) The HE ligation product is a 3' extended adaptor oligonucleotide attached to the 3' end of fragments. (FIG. 3B) One strategy for "repairing" the initial ligation product is to add a repair oligonucleotide (top strand; green); T4 polynucleotide kinase can add a phosphate (P) to the 5' end of the target fragment, and a nick sealing ligase such as Taq DNA ligase can be used to ligate the repair oligonucleotide to the target fragment. (FIG. 3C) An alternative strategy is to combine the complementary adaptor oligonucleotide, a DNA polymerase that has 5' to 3' exonuclease activity (e.g., BstI DNA polymerase), and a Taq DNA ligase. The BstI DNA polymerase extends the repair oligonucleotide by removing 5' bases from the target fragment to expose 5' phosphates that enable nick-sealing ligation by the Taq DNA ligase. (FIG. 3D) Complementary adaptor oligonucleotides can also be designed to introduce additional sequence features into the original HE ligation strand with the BstI DNA polymerase.

(FIG. 4A) DNA fragments can possess heterogeneous, "ragged" ends that may or may not possess phosphate groups (P). Treatment of the DNA fragments with a phosphatase removes exposed 5' and 3' phosphates. The DNA can then be treated with enzymes that repair DNA damage such as deaminated cytosines (U), abasic sites (↑), and thymine dimers, and that "polish" 5' or 3' overhangs to blunt ends. (FIG. 4B) Adaptors are added to DNA fragments in two steps. First, a duplex adaptor comprising a 5' phosphorylated ligation strand and a 3' blocked partner strand is ligated to the target fragments. The partner strand, which has a melting temperature of ~30° C., is removed in subsequent steps that occur at temperatures≥37° C. Second, repair oligonucleotides are annealed to the adaptor ligated fragments; the repair oligonucleotides become covalently attached to the 5' end of the target fragment either using a kinase/ligase strategy or a polymerase/exonuclease/ligase strategy (FIG. 3). Primer extension of the initial ligation strand copies the repair oligo information into a full-length adaptor duplex that is suitable for downstream analysis.

DETAILED DESCRIPTION

A. Overview

The present invention contemplates, in part, compositions and methods to address the acute need in the field of quantitative genetic analyses for improved, highly-efficient methods to clone such DNA fragments for downstream analysis.

Current methods for DNA analysis comprise ligation of specialized adaptors to DNA fragments (FIG. 1). In conventional techniques, target DNA fragments are 5' phosphorylated prior to DNA ligation to enable covalent ligation with unphosphorylated duplex adapters. The target DNA fragment and adaptor may be blunt-ended, or they may share complementary overhangs (e.g., T/A). (FIG. 1A). This is a serious drawback because it is not possible to ensure that both ends of all target DNA fragments are phosphorylated, and unphosphorylated ends are incapable of ligation and these target fragments are lost from subsequent libraries. (FIG. 1B). By way of a non-limiting example, if 70% of target DNA fragment ends possess a 5' phosphate, then only 49% of fragments (0.7×0.7×100%) at the maximum, could be ligated on both ends of the fragment and ligation to both ends is required for cloning. Additionally, the presence of 5' phosphates on target DNA fragments promotes a separate undesirable artifact in which DNA fragments can ligate to one another (FIG. 1C). This creates artifactual chromosomal sequence fusion events that can confound detection of disease-specific chromosomal rearrangements.

Figure 1A:
FIG. 1A-FIG. 1F show conventional versus high efficiency (HE) ligation technology.
Figure 1B:
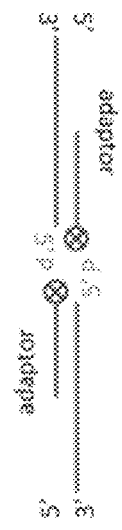
Figure 1C:
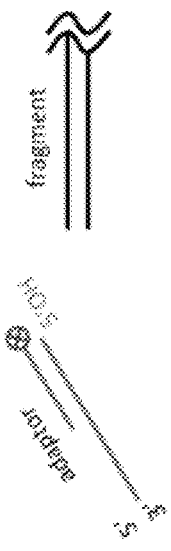
Figure 1D:
Figure 1E:
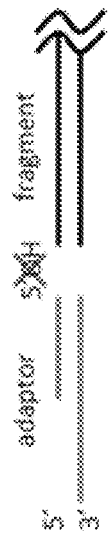
Figure 1F:
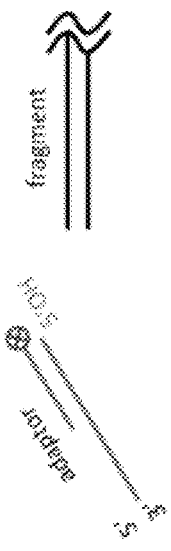

In various embodiments, the present invention contemplates, in part, compositions and methods for efficiently attaching adaptor sequences to target DNA fragments. In particular embodiments, phosphates are removed from both the 5' and 3' termini of target DNA fragments. These dephosphorylated fragments are then treated with enzymes that create blunt DNA ends and optionally with enzymes that repair many types of DNA damage that may have been inflicted on the DNA, e.g., deaminated cytosine (Uracil), an abasic site, methylation of guanine to $O^6MeG$, nicks, double strand breaks, or a thymine dimer. The adaptor comprises a ligation strand oligonucleotide duplexed with a non-ligation partner strand oligonucleotide. The ligation strand of the adaptor carries the 5' phosphate group required for ligation to target DNA fragments and the partner strand comprises a 3' blocking group (FIG. 1D). The 3' blocking group prevents the formation of adaptor:adaptor dimers (FIG. 1E). As with DNA fragments, not all adaptor sequences will possess a 5' phosphate (solvent exposed terminal phosphate bonds are inherently chemically labile). While such unphosphorylated adaptors will be present, they will only transiently engage the ligation machinery (FIG. 1F); unproductive pairing of such adaptors with fragments rapidly dissociate and are replaced by adaptor:target DNA fragment pairings that can provide productive covalent attachment. Eventually ~100% of target DNA fragments become attached on both ends with adaptor molecules, which illustrates the high efficiency of the compositions and methods contemplated herein for constructing DNA libraries.

In various embodiments, compositions and methods contemplated herein for high efficiency construction of DNA libraries provide a novel comprehensive framework address molecular genetic analysis using DNA available from a variety of biological sources. Cloning of purified DNA introduces tagged DNA sequences that inform downstream analysis and enable amplification of the resulting clone libraries. Hybrid capture with target specific oligonucleotides is used to retrieve specific sequences for subsequent analysis. Independent measurements of the number of genomes present in the library are applied to each sample, and these assays provide a means to estimate the assay's sensitivity. The assays contemplated herein provide reliable, reproducible, and robust methods for the analysis, detection, diagnosis, or monitoring of genetic states, conditions, or disease.

The practice of particular embodiments of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); and Harlow and Lane, *Antibodies*, (Cold Spring Harbor Laboratory Press, Cold Spring Harbor, N.Y., 1998).

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "isolated" means material that is substantially or essentially free from components that normally accompany it in its native state. In particular embodiments, the term "obtained" or "derived" is used synonymously with isolated.

As used herein, the term "DNA" refers to deoxyribonucleic acid. In various embodiments, the term DNA refers to genomic DNA, recombinant DNA, synthetic DNA, complementary DNA (cDNA), or cell-free DNA (cfDNA). In one embodiment, DNA refers to genomic DNA or cDNA. In one embodiment, DNA refers to cfDNA. In particular embodiments, the DNA is a DNA fragment that comprises a "target region," which is also referred to as a target DNA fragment in certain embodiments. DNA libraries contemplated herein include genomic DNA libraries, cfDNA libraries, and cDNA libraries constructed from RNA, e.g., an RNA expression library. In various embodiments, the DNA libraries comprise one or more additional DNA sequences and/or tags.

A "target genetic locus" or "DNA target region" refers to a region of interest within a DNA sequence. In various embodiments, targeted genetic analyses are performed on the target genetic locus. In particular embodiments, the DNA target region is a region of a gene that is associated with a particular genetic state, genetic condition, genetic diseases; fetal testing; genetic mosaicism, paternity testing; predicting response to drug treatment; diagnosing or monitoring a medical condition; microbiome profiling; pathogen screening; or organ transplant monitoring.

As used herein, the terms "circulating DNA," "circulating cell-free DNA" and "cell-free DNA" are often used interchangeably and refer to DNA that is extracellular DNA, DNA that has been extruded from cells, or DNA that has been released from necrotic or apoptotic cells.

A "subject," "individual," or "patient" as used herein, includes any animal that exhibits a symptom of a condition that can be detected or identified with compositions contemplated herein. Suitable subjects include laboratory animals (such as mouse, rat, rabbit, or guinea pig), farm animals (such as horses, cows, sheep, pigs), and domestic animals or pets (such as a cat or dog). In particular embodiments, the subject is a mammal. In certain embodiments, the subject is a non-human primate and, in preferred embodiments, the subject is a human.

A "reaction vessel" means a container suitable for carrying out one of the reactions contemplated herein. Illustrative examples of reaction vessels suitable for use in particular embodiments include, but are not limited to test tubes, microfuge tubes (e.g., PCR tubes), microtitre plates (e.g., 96 well plates, 384 well plates, 1536 well plates), slides, plates, arrays, and microarrays.

C. High Efficiency Construction Of DNA Library

In particular embodiments, methods of constructing DNA libraries contemplated herein comprise high efficiency ligation of adaptors to target DNA fragments.

(a) DNA Source

The methods and compositions contemplated herein are designed to efficiently analyze, detect, diagnose, and/or monitor genetic states, genetic conditions, genetic diseases, genetic mosaicism, fetal diagnostics, paternity testing, microbiome profiling, pathogen screening, and organ transplant monitoring using DNA as an analyte. DNA suitable for use in the compositions and methods contemplated herein can come from any source known to those of skill in the art. In particular embodiments, the DNA is genomic DNA isolated from any source, copy DNA (cDNA) synthesized from RNA, or cell-free DNA (cfDNA).

In some embodiments, the DNA is high molecular weight DNA (>1000 bp). Use of high molecular weight DNA in the compositions and methods contemplated herein often comprises a fragmentation step. The high molecular weight DNA can be fragmented to about 25 to about 750 base pairs, about 25 to about 500 base pairs, about 25 to about 250 base pairs, about 25 to about 200 base pairs, about 25 to about 150 base pairs, about 25 to about 100 base pairs, about 25 to about 50 base pairs, about 100 to about 200 base pairs, about 150 to about 180 base pairs, about 150 base pairs, about 155 base pairs, about 160 base pairs, about 165 base pairs, about 170 base pairs, about 175 base pairs, or about, about 180 base pairs.

Illustrative methods for fragmenting DNA suitable for use in particular embodiments of the compositions and methods contemplated herein include, but are not limited to: shearing, sonication, enzymatic digestion; including restriction digests, as well as other methods. In particular embodiments, any method known in the art for fragmenting DNA can be employed with the present invention.

Illustrative sources of genomic DNA and RNA (to generate cDNA) suitable for use in particular embodiments of the compositions and methods contemplated herein include, but are not limited to biological samples selected from the group consisting of: brain tissue, bone tissue, ocular tissue, olfactory tissue, muscles tissue, heart tissue, lung tissue, liver tissue, pancreatic tissue, kidney tissue, gastric tissue, intestinal tissue, colon tissue, blood, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy sample, and the like.

In particular embodiments, the DNA is cfDNA. The size distribution of cfDNA ranges from about 150 bp to about 180 bp fragments. Fragmentation may be the result of endonucleolytic and/or exonucleolytic activity and presents a formidable challenge to the accurate, reliable, and robust analysis of cfDNA. Another challenge for analyzing cfDNA is its short half-life in the blood stream, on the order of about 15 minutes. Without wishing to be bound to any particular theory, the present invention contemplates, in part, that analysis of cfDNA is like a "liquid biopsy" and is a real-time snapshot of current biological processes.

In some embodiments, cfDNA isolated from the blood plasma fraction can be substantially contaminated with long (>10 kilobase pair), high-molecular weight genomic DNA that is liberated from nucleated blood cells that lyse during the collection protocol. This long, contaminating DNA, if left unfragmented, does not clone and amplify well and is therefore lost during downstream library preparation. However, in particular embodiments, in the absence of DNA fragmentation, the high-efficiency DNA library construction methods contemplated herein selectively clones shorter (<1000 bp) fragments from a collection of fragment sizes present in a DNA specimen. Without wishing to be bound by any particular theory, the selective cloning of short cfDNA fragments from a DNA specimen that is a blend of long and short fragments is advantageous in the construction of a liquid biopsy.

Illustrative examples of biological samples that are suitable sources from which to isolate cfDNA in particular embodiments include, but are not limited to amniotic fluid, blood, plasma, serum, semen, lymphatic fluid, cerebral spinal fluid, ocular fluid, urine, saliva, mucous, and sweat.

In particular embodiments, the biological sample is blood or blood plasma.

In certain embodiments, the DNA sample could be derived from embedded tissues such as FFPE or fine needle aspirates, from swabs intended to interrogate microbiome sequences present, from forensic samples such as hair, clothing, fingerprints, etc. or from any other source of DNA requiring the library construction methods contemplated herein that are especially efficient for constructing libraries from low-input DNA samples.

In certain embodiments, commercially available kits and other methods known to the skilled artisan can used to isolate cfDNA directly from the biological samples of a patient or from a previously obtained and optionally stabilized biological sample, e.g., by freezing and/or addition of enzyme chelating agents including, but not limited to EDTA, EGTA, or other chelating agents specific for divalent cations.

(b) Dephosphorylation of Input DNA

Figure 4A:
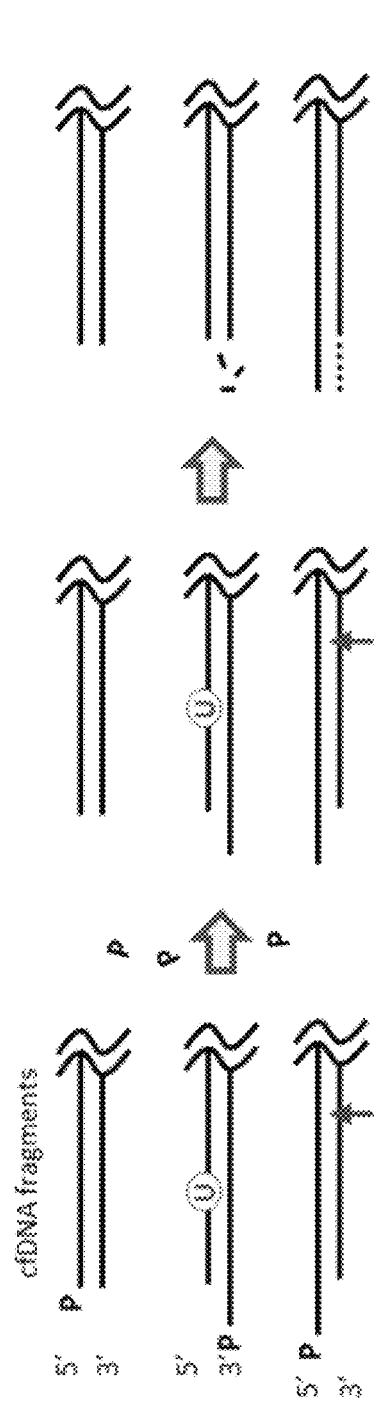
FIG. 4A-FIG. 4B show the preparation of DNA libraries using HE ligation technology.

In particular embodiments, the input DNA, e.g., target DNA fragments, is first treated with a thermo-labile phosphatase that removes terminal phosphate residues. See, e.g., FIG. 4A.

Illustrative examples of thermo-labile phosphatases that are suitable for use in particular embodiments of the compositions and methods contemplated herein include, but are not limited to APex™ Heat-Labile Alkaline Phosphatase (Epicentre Biotechnologies), NTPhos™ Thermolabile Phosphatase (Epicentre Biotechnologies), HK™ Thermolabile Phosphatase (Epicentre Biotechnologies), and Shrimp Alkaline Phosphatase (SAP; NEB).

In one embodiment, the thermo-labile phosphatase is SAP.

(c) Reversing DNA Damage in the Target DNA Fragments

In particular embodiments, the input DNA or dephosphorylated DNA is also treated with one or more enzymes that reverse common sources of DNA damage such as deamination of cytosines to uracil, oxidative addition to guanines, thymidine dimers, loss of bases leading to abasic sites, nicks or gaps on one strand of duplex DNA, etc. See, e.g., FIG. 4A.

In one embodiment, the internal damage to the DNA is reversed using a composition comprising one or more of the following enzymes: Taq DNA Ligase, Endonuclease IV, Bst DNA Polymerase, Fpg (8-oxoguanine DNA glycosylase), Uracil-DNA Glycosylase (UDG), T4 PDG (T4 Endonuclease V), Endonuclease VIII, and T4 DNA polymerase.

In one embodiment, the internal damage to the DNA is reversed using a composition comprising Taq DNA Ligase, Endonuclease IV, Bst DNA Polymerase, Fpg, Uracil-DNA Glycosylase (UDG), T4 PDG (T4 Endonuclease V), Endonuclease VIII, and T4 DNA polymerase.

(d) Generating End-Repaired DNA

In particular embodiments, the compositions and methods contemplated herein comprise generating end-repaired DNA fragments. In certain embodiments, the DNA fragments are end-repaired to generate end-repaired DNA fragments with blunt ends, 5'-overhangs, or 3'-overhangs. See, e.g., FIG. 4A. In particular embodiments, the DNA is cfDNA.

In some embodiments, the end-repaired DNA contains blunt ends. In some embodiments, the end-repaired DNA is processed to contain blunt ends. In preferred embodiments, the DNA fragments are end-repaired by one or more end-repair enzymes to generate end-repaired DNA fragments with blunt ends.

Illustrative examples of end-repair enzymes suitable for generating blunt-ended DNA fragments in particular embodiments of the compositions and methods contemplated herein include DNA polymerases which retains polymerization activity and 3'→5' exonuclease activity, but that lacks 5'→3' exonuclease activity (e.g., T4 DNA polymerase, Klenow fragment of DNA polymerase I, etc.). The DNA polymerase is used to either fill in 5' overhangs or "chew back" 3' overhangs, leaving the DNA fragments with blunt ends.

In some embodiments, the blunt ends of the end-repaired DNA are further modified to contain a single base pair overhang. In some embodiments, end-repaired DNA containing blunt ends can be further processed to contain adenine (A)/thymine (T) overhang. In some embodiments, end-repaired DNA containing blunt ends can be further processed to contain adenine (A)/thymine (T) overhang as the single base pair overhang. In some embodiments, the end-repaired DNA has non-templated 3' overhangs. In some embodiments, the end-repaired DNA is processed to contain 3' overhangs. In some embodiments, the end-repaired DNA is processed with terminal transferase (TdT) to contain 3' overhangs. In some embodiments, a G-tail can be added by TdT. In some embodiments, the end-repaired DNA is processed to contain overhang ends using partial digestion with any known restriction enzymes (e.g., with the enzyme Sau3A, and the like).

(e) Ligating Pre-Adaptors to End-Repaired DNA

In particular embodiments, the compositions and methods contemplated herein comprise ligating a duplex DNA pre-adaptor to each end of the end-repaired DNA.

Figure 4B:
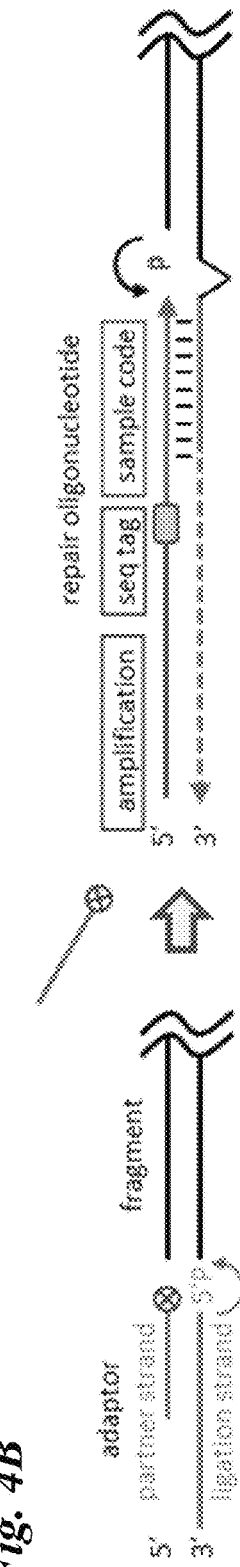
Figure 5:
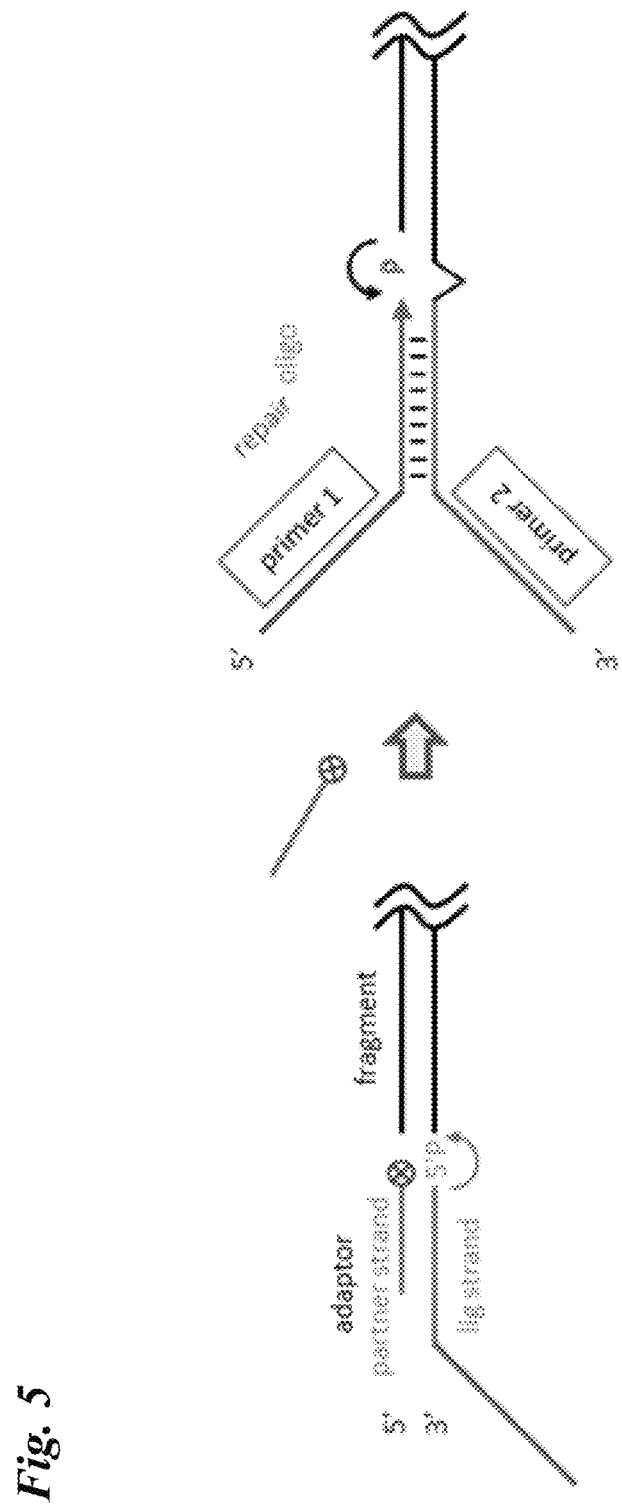
FIG. 5 shows a HE ligation technology strategy for generating dual PCR primer adapted DNA fragments. In this scheme, the ligation strand carries additional sequences (primer 2) that serve as an independent primer binding site. The repair oligonucleotide, while complementary to a portion of the ligation strand, has its own divergent sequence that serves as a second PCR primer binding site (primer 1). The fully completed adaptors allow amplification of the DNA specimen fragments using more conventional, universal dual-primer PCR methods.

As used herein, the term "pre-adaptor" refers to a double-stranded DNA molecule or DNA duplex that comprises a ligation strand oligonucleotide and a partner strand oligonucleotide. The pre-adapter may be ligated to the end-repaired DNA fragments using any suitable ligase. In one embodiment, the ligase is T4 DNA ligase. See, e.g., FIGS. 4B and 5.

The "ligation strand oligonucleotide" is a polynucleotide that comprises a 5' phosphate and is capable of being ligated to each 3' end of the end-repaired DNA fragment.

The "partner strand oligonucleotide" is complementary to, and anneals to, a portion of, or to all of, the nucleotides of the ligation strand oligonucleotide. The partner strand oligonucleotide comprises a modification at its 3' end that prevents or substantially inhibits the partner strand oligonucleotide from being ligated to another adapter or to a phosphorylated 5' end of a target DNA fragment. Chemical modifications of the 3' end of the partner stand that can block ligation include, but are not limited to dideoxy ribose nucleotide analogs, 2-hydroxyl deoxyribose ribose analogs, and a broad variety of chemical modification to the ribose sugar.

Several considerations go into the sequence design and content of the ligation strand oligonucleotides used in the pre-adaptor. The ligation strand oligonucleotide can vary in length from the minimum length required to form a stable DNA duplex at temperatures where DNA ligase is active (~5 nt) to oligonucleotides that push the limits of current synthesis capabilities (>200 nt). In particular embodiments, the ligation strand oligonucleotide is about 8 to about 60 nucleotides or about 8 to about 15 nucleotides.

As an additional consideration related to the NGS analysis of DNA fragments, the DNA bases incorporated by the ligation strand are used by the sequencing instrument to calibrate DNA base calls throughout the DNA sequencing run. The instrument and software of these instruments require that all four DNA bases be present at every base position throughout the length of the initial 8-15 nucleotides sequenced, and this often includes bases embedded in the ligation adaptor strand. For this reason, sets of four ligation strands that mutually possess all four bases across the length of the ligation strand sequence are often used. Non-limiting examples of such ligation strand oligonucleotides are shown in Tables 1 and 2.

In various other embodiments, the ligation strand oligonucleotide comprises the following elements: (i) a PCR primer binding site for the single-primer library amplification; (ii) a 5 nucleotide read code that acts to uniquely identified each sequencing read; (iii) an 8 to 15 nucleotide anchor sequence that acts as a sample identification sequence, enables sample multiplexing within a sequencing run; enables calibration of proper base calls in sequencing reads, and acts as an anchor for hybridization to a partner strand oligonucleotide.

In various other embodiments, the ligation strand oligonucleotide comprises an 8 to 15 nucleotide anchor sequence that acts as a sample identification sequence, enables sample multiplexing within a sequencing run; enables calibration of proper base calls in sequencing reads, and acts as an anchor for hybridization to a partner strand oligonucleotide.

In particular embodiments, a ligation strand oligonucleotide comprises one or more PCR primer sequences, one or more read codes, one or more sample codes, one or more anchor sequences, or two or more 3' nucleotides that are efficient ligation substrates. In additional embodiments, the ligation strand oligonucleotide further comprises one or more sequencing primer binding sites.

In particular embodiments, a ligation strand oligonucleotide comprises one or more PCR primer binding sequences for amplification of a DNA library. In one embodiment, the PCR primer binding sequence is about 12 to about 40 nucleotides, about 18 to about 40 nucleotides, about 20 to about 35 nucleotides, or about 20 to about 30 nucleotides. In another embodiment, the PCR primer binding sequence is about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, or about 40 nucleotides or more.

In one embodiment, the PCR primer binding sequence is about 25 nucleotides.

In particular embodiments, a ligation strand oligonucleotide comprises one or more read code sequences. As used herein, the term "read code" refers to a polynucleotide that is used to identify unique sequencing reads. In one embodiment, the read code is a random sequence of nucleotides. In one embodiment, the read code is about 1 nucleotide, about 2 nucleotides, about 3 nucleotides, about 4 nucleotides, about 5 nucleotides, about 6 nucleotides, about 7 nucleotides, about 8 nucleotides, about 9 nucleotides, about 10 nucleotides, or more.

By way of a non-limiting example, a 5 nucleotide read code consists of 256 possible unique sequences where each code chosen is 2 nucleotides different from every other code in the set. This feature enables unique and distinct reads to be differentiated from reads that appear to be unique owing to a sequencing error in the code region. In particular embodiments, codes that have been empirically determined to interfere with adaptor function, owing to particular sequence combinations, may be excluded from use, e.g., seven codes of the 256 had an overrepresentation of G nucleotides and were excluded.

In other embodiments, each read code of 5, 6, 7, 8, 9, 10 or more nucleotides may differ by 2, 3, 4, or 5 nucleotides from every other read code.

In one embodiment, the read code is about 5 nucleotides and optionally, differs from every other read code by 2 nucleotides.

In particular embodiments, a ligation strand oligonucleotide comprises one or more sample code sequences. As used herein, the term "sample code" refers to a polynucleotide that is used to identify the sample. The sample code is also useful in establishing multiplex sequencing reactions because each sample code is unique to the sample and thus, can be used to identify a read from a particular sample within a multiplexed sequencing reaction.

In one embodiment, the sample code comprises sequence that is about 1, about 2 nucleotides, about 3 nucleotides, about 4 nucleotides, or about 5 nucleotides, or more. In another embodiment, each sample code of 2, 3, 4, 5 or more nucleotides may differ from every other sample code by 2, 3, 4, or 5 nucleotides.

In one embodiment, the sample code is about three nucleotides and differs from every other sample code used in other samples by two nucleotides.

In particular embodiments, a ligation strand oligonucleotide comprises a one or more anchor sequences. As used herein, an "anchor sequence" refers to a nucleotide sequence of at least 8 nucleotides, at least 10 nucleotides, at least 12 nucleotides, at least 14 nucleotides, or at least 16 nucleotides that hybridizes to a partner strand oligonucleotide and that comprises the following properties: (1) each anchor sequence is part of a family of four anchor sequences that collectively represent each of the four possible DNA bases at each site within extension; this feature, balanced base representation, is useful to calibrate proper base calling in sequencing reads in particular embodiments; and (2) each anchor sequence is composed of equal numbers of A+C and G+T, and thus, each anchor sequence shares roughly the same melting temperature and duplex stability as every other anchor sequence in a set of four. In one embodiment, the anchor sequence or a portion thereof also serves to identify the sample, enables sample multiplexing within a sequencing run, enable calibration of proper base calls in sequencing reads, and act as an anchor for hybridization to a partner strand oligonucleotide.

In addition, several considerations are involved in the design of the non-ligating partner strand oligonucleotide. The partner strand oligonucleotide is at least partially complementary (>5 nt) to the ligation strand oligonucleotide in the region that forms the phosphorylated blunt end. Second, the 3' end of the partner strand oligonucleotide is modified to block or substantially inhibit the oligonucleotide from becoming a ligation substrate, particular in the formation of self-ligated adaptor dimers. The partner strand oligonucleotide is designed to form a stable duplex with the ligation strand at temperatures where ligations are performed ($\leq 22°$ C.) but is also designed to dissociate from the ligation strand oligonucleotide at temperatures where a repair oligonucleotide is incorporated into the adaptor ($\geq 37°$ C.). This design consideration is depicted as the dissociated partner strand oligonucleotide shown in FIGS. 4B and 5 in the generation of the adaptor/end-repaired DNA complexes, as the reaction is shifted from ligation to the adaptor completion step that is mediated by repair oligonucleotides.

In particular embodiments, the compositions and methods contemplated herein comprise a ligation step wherein a pre-adaptor is ligated to the end-repaired DNA to generate a "tagged" DNA library. In some embodiments, a single species of pre-adaptor is employed. In some embodiments, two, three, four or five species of pre-adaptors are employed. In some embodiments, a pre-adaptor of identical sequence is ligated to each end of the fragmented end-repaired DNA.

In one embodiment, a plurality of pre-adaptor species is ligated to an end-repaired DNA library. Each of the plurality of pre-adaptors may comprise one or more primer binding site for amplification of the DNA library, one or more read code sequences, one or more sequences for sample multiplexing, one or more anchor sequences, or one or more sequences for DNA sequencing.

(f) Formation of Adaptor/End-Repaired DNA Complexes

In particular embodiments, the compositions and methods contemplated herein comprise displacing the partner strand oligonucleotide from the pre-adaptor/end-repaired DNA complex and replacing the displaced partner strand oligonucleotide with a repair oligonucleotide to generate an adaptor/end-repaired DNA complex. See, e.g., FIG. 3. In particular embodiments, the design of the adaptor can be manipulated to enable single primer or dual primer amplification strategies. See, e.g., FIGS. 4A, and 5.

In particular embodiments, the compositions and methods contemplated herein comprise a ligation step wherein an adaptor comprising a ligation strand oligonucleotide and a repair oligonucleotide is ligated to the end-repaired DNA to generate a "tagged" DNA library. In some embodiments, a single species of adaptor is employed. In some embodiments, two, three, four or five species of adaptors are employed. In some embodiments, an adaptor of identical sequence is ligated to each end of the fragmented end-repaired DNA.

The design considerations of the partner strand oligonucleotide allow it to be displaced from the pre-adaptor/end-repaired DNA complex because it dissociates from the ligation strand oligonucleotide at temperatures at which the repair oligonucleotide anneals to the ligation strand oligonucleotide (e.g., >37° C.) and at temperatures at which the enzymatic steps are carried out to incorporate the repair oligonucleotide into an adaptor/end-repaired DNA complex generate a contiguous, double-stranded, DNA library molecule (e.g., >37° C.).

As used herein, the term "repair oligonucleotide" refers to a polynucleotide sequence that is complementary to, and anneals to, a portion of, or to all of, the nucleotides of the ligation strand oligonucleotide. The repair oligonucleotide can vary in length from the minimum length required to form a stable DNA duplex at temperatures where DNA ligase is active (~8 nt) to oligonucleotides that push the limits of current synthesis capabilities (>200 nt). In particular embodiments, the "repair oligonucleotide" includes additional, functional DNA sequences that are not necessarily present in the ligation strand oligonucleotide.

In particular embodiments, the ligation strand oligonucleotide is about 8 to about 15 nucleotides and the repair oligonucleotide is 35 to 60 nucleotides. In this design, the sequence of the ligand strand oligonucleotide is extended by primer extension and generates a nucleotide sequence complementary to the repair oligonucleotide. This design would yield identical PCR primer binding sites. Identical PCR primer binding sites allows for a single primer library amplification strategy. See, e.g., FIGS. 3D and 4A.

In particular embodiments, the ligation strand oligonucleotide is about 35 to about 60 nucleotides and the repair oligonucleotide is completely complementary to the ligation strand oligonucleotide. Identical PCR primer binding sites allows for a single primer library amplification strategy. See, e.g., FIG. 4A.

In particular embodiments, the ligation strand oligonucleotide is about 35 to about 60 nucleotides and the repair oligonucleotide is about 35 to about 60 nucleotides and the two oligonucleotides are complementary but for the PCR primer binding sites. Different PCR primer binding sites allows for a dual primer library amplification strategy. See, e.g., FIG. 5.

In preferred embodiments, the ligation strand oligonucleotide comprises the following elements: (i) a PCR primer binding site for the single-primer library amplification; (ii) a 5 nucleotide read code that acts to uniquely identified each sequencing read; (iii) an 8 to 15 nucleotide anchor sequence that is partially or completely complementary to the anchor sequence of the ligation strand oligonucleotide.

In other embodiments, the ligation strand oligonucleotide comprises an 8 to 15 nucleotide anchor sequence that is partially or completely complementary to the anchor sequence of the ligation strand oligonucleotide.

In particular embodiments, a repair oligonucleotide comprises one or more PCR primer sequences, one or more read codes, one or more sample codes, one or more anchor sequences, or two or more 3' nucleotides that are efficient ligation substrates. In additional embodiments, the repair oligonucleotide further comprises one or more sequencing primer binding sites.

In particular embodiments, a repair oligonucleotide comprises (i) one or more PCR primer binding sequences that are complementary to the PCR primer binding sites in the ligation strand oligonucleotide (enables single-primer DNA library amplification) or (ii) one or more PCR primer binding sequences that are not complementary to the PCR primer binding sites in the ligation strand oligonucleotide (enables dual-primer DNA library amplification. In one embodiment, the PCR primer binding sequence is about 12 to about 40 nucleotides, about 18 to about 40 nucleotides, about 20 to about 35 nucleotides, or about 20 to about 30 nucleotides. In another embodiment, the PCR primer binding sequence is about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, or about 40 nucleotides or more.

In one embodiment, the PCR primer binding sequence is about 25 nucleotides.

In particular embodiments, a repair oligonucleotide comprises one or more read code sequences. In one embodiment, the read code is a random sequence of nucleotides. In one embodiment, the read code is about 1 nucleotide, about 2 nucleotides, about 3 nucleotides, about 4 nucleotides, about 5 nucleotides, about 6 nucleotides, about 7 nucleotides, about 8 nucleotides, about 9 nucleotides, about 10 nucleotides, or more.

By way of a non-limiting example, a 5 nucleotide read code consists of 256 possible unique sequences where each code chosen is 2 nucleotides different from every other code in the set. This feature enables unique and distinct reads to be differentiated from reads that appear to be unique owing to a sequencing error in the code region. In particular embodiments, codes that have been empirically determined to interfere with adaptor function, owing to particular sequence combinations, may be excluded from use, e.g., seven codes of the 256 had an overrepresentation of G nucleotides and were excluded.

In other embodiments, each read code of 5, 6, 7, 8, 9, 10 or more nucleotides may differ by 2, 3, 4, or 5 nucleotides from every other read code.

In one embodiment, the read code is about 5 nucleotides and optionally, differs from every other read code by 2 nucleotides.

In particular embodiments, a repair oligonucleotide comprises one or more sample code sequences. In one embodiment, the sample code comprises sequence that is about 1, about 2 nucleotides, about 3 nucleotides, about 4 nucleotides, or about 5 nucleotides, or more. In another embodiment, each sample code of 2, 3, 4, 5 or more nucleotides may differ from every other sample code by 2, 3, 4, or 5 nucleotides.

In one embodiment, the sample code is about three nucleotides and differs from every other sample code used in other samples by two nucleotides.

In particular embodiments, a repair oligonucleotide comprises a one or more anchor sequences complementary to the one or more anchor sequences of the ligation strand oligonucleotide.

Without wishing to be bound by any particular theory, at least two exemplary strategies are contemplated for incorporating the repair oligonucleotide into an adaptor/end-repair DNA complex.

In one embodiment, the partner strand oligonucleotide is displaced from the pre-adaptor/end-repaired DNA complex; repair oligonucleotide is added and allowed to anneal to the ligation strand; polynucleotide kinase, e.g., T4 polynucleotide kinase, is used to add a phosphate group to the 5' end of the end-repaired DNA fragment; and DNA ligase is used to repair the nick that exists between the 5' end of the repair oligonucleotide and the 3' end of the end-repaired DNA fragment. In particular embodiments, the DNA ligase is a thermo-stable nick-specific ligase that has activity across a broad range of temperatures, including, but not limited to Taq DNA ligase, E. coli DNA ligase, 9° North ligase (NEB), and any other ligase that can seal a phosphorylated nick. See, e.g., FIGS. 3A and 3B.

In another embodiment, the partner strand oligonucleotide is displaced from the pre-adaptor/end-repaired DNA complex; repair oligonucleotide is added and allowed to anneal to the ligation strand; a low processivity DNA polymerase that has a 5'→3' exonuclease activity (and no intrinsic 3'→5' exonuclease activity) extends the 3' end of ligation strand oligonucleotide and in addition, removes the dephosphorylated 5' terminal nucleotide and adjacent nucleotides with a 5'→3' exonuclease activity thereby exposing ligatable 5' phosphate groups and replacing them with incorporated bases that leave behind a nick when the enzyme dissociates; and DNA ligase, e.g., Taq DNA ligase, is used to repair the nicks.

Illustrative examples of low processivity DNA polymerases suitable for use in particular embodiments of the compositions and methods contemplated herein include, but are not limited to Taq DNA polymerase, and BstI DNA polymerase.

D. DNA Library Amplification

In particular embodiments, methods contemplated herein comprise amplification of a DNA library to generate a DNA clone library or a library of DNA clones. In particular embodiments, the DNA is cfDNA. Each molecule of the DNA library comprises an adaptor ligated to each end of an end-repaired DNA, and each adaptor comprises one or more PCR primer binding sites. In one embodiment, different adaptors are ligated to different ends of the end-repaired DNA.

In one embodiment, the same adaptor is ligated to both ends of the DNA. Ligation of the same adaptor to both ends of end-repaired DNA allows for PCR amplification with a single primer sequence. In particular embodiments, a portion of the adaptor ligated-DNA library will be amplified using standard PCR techniques with a single primer sequence driving amplification. In one embodiment, the single primer sequence is about 25 nucleotides, optionally with a projected Tm of ≥55° C. under standard ionic strength conditions.

In one embodiment, the adaptor ligated to the 3' end of an end-repaired DNA fragment comprises a different PCR primer binding site from the adaptor ligated to the 5' end of the end-repaired DNA fragment. In particular embodiments, a portion of the adaptor ligated-DNA library will be amplified using standard PCR techniques with two primers riving amplification.

In particular embodiments, picograms of the initial DNA library are amplified into micrograms of DNA clones, implying a 10,000-fold amplification. The amount of amplified product can be measured using methods known in the art, e.g., quantification on a Qubit 2.0 or Nanodrop instrument.

E. Methods of Genetic Analysis of DNA

In various embodiments, a method for genetic analysis of DNA is provided. In particular embodiments, the DNA is cfDNA. cfDNA is cell-free DNA that is found in plasma or other bodily fluids.

In particular embodiments, a method for genetic analysis of DNA comprises: generating and amplifying a DNA library, determining the number of genome equivalents in the DNA library; and performing a quantitative genetic analysis of one or more genomic target loci.

1. Determining the Number of Genome Equivalents

In various embodiments, a method for genetic analysis of DNA comprises determining the number of genome equivalents in the DNA clone library. As used herein, the term "genome equivalent" refers to the number of genome copies in each library. An important challenge met by the compositions and methods contemplated herein is achieving sufficient assay sensitivity to detect and analysis rare genetic mutations or differences in genetic sequence. To determine assay sensitivity value on a sample-by-sample basis, the numbers of different and distinct sequences that are present in each sample are measured, by measuring the number of genome equivalents that are present in a sequencing library. To establish sensitivity, the number of genome equivalents must be measured for each sample library.

The number of genome equivalents can be determined by qPCR assay or by using bioinformatics-based counting after sequencing is performed. In the process flow of clinical samples, qPCR measurement of genome equivalents is used as a QC step for DNA libraries. It establishes an expectation for assay sensitivity prior to sequence analysis and allows a sample to be excluded from analysis if its corresponding DNA clone library lacks the required depth of genome equivalents. Ultimately, the bioinformatics-based counting of genome equivalents is also used to identify the genome equivalents—and hence the assay sensitivity and false negative estimates—for each given DNA clone library.

The empirical qPCR assay and statistical counting assays should be well correlated. In cases where sequencing fails to reveal the sequence depth in a DNA clone library, reprocessing of the DNA clone library and/or additional sequencing may be required.

In one embodiment, the genome equivalents in a DNA clone library are determined using a quantitative PCR (qPCR) assay. In a particular embodiment, a standard library of known concentration is used to construct a standard curve and the measurements from the qPCR assay are fit to the resulting standard curve and a value for genome equivalents is derived from the fit. The number of genome equivalents measured by the repeat-based assays provides a more consistent library-to-library performance and a better alignment between qPCR estimates of genome equivalents and bioinformatically counted tag equivalents in sequencing runs.

Illustrative examples of repeats suitable for use in the repeat-based genome equivalent assays contemplated herein include, but are not limited to: short interspersed nuclear elements (SINEs), e.g., Alu repeats; long interspersed nuclear elements (LINEs), e.g., LINE1, LINE2, LINE3; microsatellite repeat elements, e.g., short tandem repeats (STRs), simple sequence repeats (SSRs); and mammalian-wide interspersed repeats (MIRs).

In one embodiment, the repeat is an Alu repeat.

2. Quantitative Genetic Analysis

In various embodiments, a method for genetic analysis of DNA comprises quantitative genetic analysis of one or more target genetic loci of the DNA library clones. Quantitative genetic analysis comprises one or more of, or all of, the following steps: capturing DNA clones comprising a target genetic locus; amplification of the captured targeted genetic locus; sequencing of the amplified captured targeted genetic locus; and bioinformatic analysis of the resulting sequence reads.

(a) Capture of Target Genetic Locus

The present invention contemplates, in part, a capture probe module that is multifunctional and designed to retain the efficiency and reliability of larger probes but that minimizes uninformative sequence generation in a DNA clone library. A "capture probe module" refers to a polynucleotide that comprises a capture probe sequence and a tail sequence. In particular embodiments, the capture probe module sequence or a portion thereof serves as a primer binding site for one or more sequencing primers.

In particular embodiments, a capture probe module comprises a capture probe. As used herein a "capture probe" refers to a polynucleotide comprising a region capable of hybridizing to a specific DNA target region. Because the average size of DNA is relatively small and is highly fragmented, the compositions and methods contemplated herein comprise the use of high density and relatively short capture probes to interrogate DNA target regions of interest.

In particular embodiments, a capture probe module is combined with a partner oligonucleotide that optionally comprises a hapten and that hybridizes the tail sequence to generate a capture probe module duplex.

One particular concern with using high density capture probes is that generally capture probes are designed using specific "sequence rules." For example, regions of redundant sequence or that exhibit extreme base composition biases are generally excluded in designing capture probes. However, the present inventors have discovered that the lack of flexibility in capture probe design rules does not substantially impact probe performance. In contrast, capture probes chosen strictly by positional constraint provided on-target sequence information; exhibit very little off-target and unmappable read capture; and yield uniform, useful, on-target reads with only few exceptions. Moreover, the high redundancy at close probe spacing more than compensates for occasional poor-performing capture probes.

In particular embodiments, a target region is targeted by a plurality of capture probes, wherein any two or more capture probes are designed to bind to the target region within 10 nucleotides of each other, within 15 nucleotides of each other, within 20 nucleotides of each other, within 25 nucleotides of each other, within 30 nucleotides of each other, within 35 nucleotides of each other, within 40 nucleotides of each other, within 45 nucleotides of each other, or within 50 nucleotides or more of each other, as well as all intervening nucleotide lengths.

In one embodiment, the capture probe is about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, or about 45 nucleotides.

In one embodiment, the capture probe is about 100 nucleotides, about 200 nucleotides, about 300 nucleotides, about 400 nucleotides, or about 100 nucleotides. In another embodiment, the capture probe is from about 100 nucleotides to about 500 nucleotides, about 200 nucleotides to about 500 nucleotides, about 300 nucleotides to about 500 nucleotides, or about 400 nucleotides to about 500 nucleotides, or any intervening range thereof.

In a particular embodiment, the capture probe is 60 nucleotides.

In a particular embodiment, the capture probe is not 60 nucleotides.

In another embodiment, the capture probe is substantially smaller than 60 nucleotides but hybridizes comparably, as well as, or better than a 60 nucleotide capture probe targeting the same DNA target region.

In a certain embodiment, the capture probe is 40 nucleotides.

In certain embodiments, a capture probe module comprises a tail sequence. As used herein, the term "tail sequence" refers to a polynucleotide at the 5' end of the capture probe module, which in particular embodiments can serve as a primer binding site. In particular embodiments, a sequencing primer binds to the primer binding site in the tail region.

In particular embodiments, the tail sequence is about 5 to about 100 nucleotides, about 10 to about 100 nucleotides, about 5 to about 75 nucleotides, about 5 to about 50 nucleotides, about 5 to about 25 nucleotides, or about 5 to about 20 nucleotides. In certain embodiments, the third region is from about 10 to about 50 nucleotides, about 15 to about 40 nucleotides, about 20 to about 30 nucleotides or about 20 nucleotides, or any intervening number of nucleotides.

In particular embodiments, the tail sequence is about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, or about 40 nucleotides.

In various embodiments, the capture probe module comprises a specific member of a binding pair to enable isolation and/or purification of one or more captured fragments of a tagged and or amplified DNA library that hybridizes to the capture probe. In particular embodiments, the capture probe module is conjugate to biotin or another suitable hapten, e.g., dinitrophenol, digoxigenin.

In various embodiments, the capture probe module is hybridized to a tagged and optionally amplified DNA library to form a complex. In some embodiments, the multifunctional capture probe module substantially hybridizes to a specific genomic target region in the DNA library.

Hybridization or hybridizing conditions can include any reaction conditions where two nucleotide sequences form a stable complex; for example, the tagged DNA library and capture probe module forming a stable tagged DNA library—capture probe module complex. Such reaction conditions are well known in the art and those of skill in the art will appreciated that such conditions can be modified as appropriate, e.g., decreased annealing temperatures with shorter length capture probes, and within the scope of the present invention. Substantial hybridization can occur when the second region of the capture probe complex exhibits 100%, 99%, 98%, 97%, 96%, 95%, 94%, 93%, 92% 91%, 90%, 89%, 88%, 85%, 80%, 75%, or 70% sequence identity, homology or complementarity to a region of the tagged DNA library.

In particular embodiments, the capture probe is about 40 nucleotides and has an optimal annealing temperature of about 44° C. o about 47° C.

In certain embodiments, the methods contemplated herein comprise isolating a tagged DNA library—capture probe module complex. In particular embodiments, methods for isolating DNA complexes are well known to those skilled in the art and any methods deemed appropriate by one of skill in the art can be employed with the methods of the present invention (Ausubel et al., *Current Protocols in Molecular Biology*, 2007-2012). In particular embodiments, the complexes are isolated using biotin—streptavidin isolation techniques. In some embodiments, the capture partner oligonucleotide capable of hybridizing to the tail sequence of the multifunctional capture probe module is modified to contain a biotin at the 5'-end or 3'-end which is capable of interacting with streptavidin linked to a column, bead or other substrate for use in DNA complex isolation methods.

In one embodiment, the capture partner oligonucleotide capable of hybridizing to the tail sequence of the multifunctional capture probe module is modified to contain a biotin at the 3'-end which is capable of interacting with streptavidin linked to a column, bead or other substrate for use in DNA complex isolation methods.

In particular embodiments, a tail sequence of a multifunctional capture probe module is bound to a capture partner oligonucleotide. In some embodiments, the multifunctional capture probe module is bound to the capture partner oligonucleotide prior to formation of a tagged DNA library—multifunctional capture probe module complex. In some embodiments, the multifunctional capture probe module is bound to the capture partner oligonucleotide after the formation of a tagged DNA library—multifunctional capture probe module complex. In some embodiments, the multifunctional capture probe module is bound to the capture partner oligonucleotide simultaneously with the formation of a tagged DNA library—multifunctional capture probe module complex. In some embodiments, the capture partner oligonucleotide is chemically modified. In one embodiment, the capture partner oligonucleotide is modified by adding a hapten to the 5' or 3' end. In one embodiment the hapten is biotin.

In particular embodiments, removal of the single stranded 3'-ends from the isolated tagged DNA library—capture probe module complex is contemplated. In certain embodiments, the methods comprise 3'-5' exonuclease enzymatic processing of the isolated tagged DNA library-multifunctional capture probe module complex to remove the single stranded 3' ends.

In certain other embodiments, the methods comprise performing 5'-3' DNA polymerase extension of multifunctional capture probe utilizing the isolated tagged DNA library fragments as template.

In certain other embodiments, the methods comprise creating a hybrid capture probe-isolated tagged DNA target molecule through the concerted action of a 5' FLAP endonuclease, DNA polymerization and nick closure by a DNA ligase.

A variety of enzymes can be employed for the 3'-5' exonuclease enzymatic processing of the isolated tagged DNA library-multifunctional capture probe module complex. Illustrative examples of suitable enzymes, which exhibit 3'-5' exonuclease enzymatic activity, that can be employed in particular embodiments include, but are not limited to: T4 or Exonucleases I, III, V (see also, Shevelev IV, Hübscher U., "The 3' 5' exonucleases," *Nat Rev Mol Cell Biol.* 3(5):364-76 (2002)). In particular embodiments, the enzyme comprising 3'-5' exonuclease activity is T4. In particular embodiments, an enzyme which exhibits 3'-5' exonuclease enzymatic activity and is capable of primer template extension can be employed, including for example T4 or Exonucleases I, III, V. Id.

In some embodiments, the methods contemplated herein comprise performing sequencing and/or PCR on the 3'-5' exonuclease enzymatically processed complex discussed supra and elsewhere herein. In particular embodiments, a tail portion of a capture probe molecule is copied in order to generate a hybrid nucleic acid molecule. In one embodiment, the hybrid nucleic acid molecule generated comprises the target region capable of hybridizing to the capture probe module and the complement of the capture probe module tail sequence.

In a particular embodiment, genetic analysis comprises a) hybridizing one or more capture probe modules to one or more target genetic loci in a plurality of DNA library clones to form one or more capture probe module-DNA library clone complexes; b) isolating the one or more capture probe module-DNA library clone complexes from a); c) enzymatically processing the one or more isolated capture probe module-DNA library clone complexes from step b); d) performing PCR on the enzymatically processed complex from c) wherein the tail portion of the capture probe molecule is copied in order to generate amplified hybrid nucleic acid molecules, wherein the amplified hybrid nucleic acid molecules comprise a target sequence in the target genomic locus capable of hybridizing to the capture probe and the complement of the capture probe module tail sequence; and e) performing quantitative genetic analysis on the amplified hybrid nucleic acid molecules from d).

In a particular embodiment, methods for determining copy number of a specific target genetic locus are contemplated comprising: a) hybridizing one or more capture probe modules to one or more target genetic loci in a plurality of DNA library clones to form one or more capture probe module-DNA library clone complexes; b) isolating the one or more capture probe module-DNA library clone complexes from a); c) enzymatically processing the one or more isolated capture probe module-DNA library clone complexes from step b); d) performing PCR on the enzymatically processed complex from c) wherein the tail portion of the capture probe molecule is copied in order to generate amplified hybrid nucleic acid molecules, wherein the amplified hybrid nucleic acid molecules comprise a target sequence in the target genetic locus capable of hybridizing to the capture probe and the complement of the capture probe module tail sequence; e) performing PCR amplification of the amplified hybrid nucleic acid molecules in d); and f) quantitating the PCR reaction in e), wherein the quantitation allows for a determination of copy number of the specific target region.

In one embodiment, the enzymatic processing of step c) comprises performing 3'-5' exonuclease enzymatic processing on the one or more capture probe module-DNA library clone complexes from b) using an enzyme with 3'-5' exonuclease activity to remove the single stranded 3' ends; creating one or more hybrid capture probe module-DNA library clone molecules through the concerted action of a 5' FLAP endonuclease, DNA polymerization and nick closure by a DNA ligase; or performing 5'-3' DNA polymerase extension of the capture probe using the isolated DNA clone in the complex as a template.

In one embodiment, the enzymatic processing of step c) comprises performing 5'-3' DNA polymerase extension of the capture probe using the isolated DNA clone in the complex as a template.

In particular embodiments, PCR can be performed using any standard PCR reaction conditions well known to those of skill in the art. In certain embodiments, the PCR reaction in e) employs two PCR primers. In one embodiment, the PCR reaction in e) employs a first PCR primer that hybridizes to a repeat within the target genetic locus. In a particular embodiment, the PCR reaction in e) employs a second PCR primer that hybridizes to the hybrid nucleic acid molecules at the target genetic locus/tail junction. In certain embodiments, the PCR reaction in e) employs a first PCR primer that hybridizes to the target genetic locus and a second PCR primer hybridizes to the amplified hybrid nucleic acid molecules at the target genetic locus/tail junction. In particular embodiments, the second primer hybridizes to the target genetic locus/tail junction such that at least one or more nucleotides of the primer hybridize to the target genetic locus and at least one or more nucleotides of the primer hybridize to the tail sequence.

In certain embodiments, the amplified hybrid nucleic acid molecules obtained from step e) are sequenced and the sequences aligned horizontally, i.e., aligned to one another but not aligned to a reference sequence. In particular embodiments, steps a) through e) are repeated one or more times with one or more capture probe modules. The capture probe modules can be the same or different and designed to target either DNA strand of a target genetic locus. In some embodiments, when the capture probes are different, they hybridize at overlapping or adjacent target sequences within a target genetic locus in the tagged DNA clone library. In one embodiment, a high density capture probe strategy is used wherein a plurality of capture probes hybridize to a target genetic locus, and wherein each of the plurality of capture probes hybridizes to the target genetic locus within about 5, 10, 15, 20, 25, 30, 35, 40, 45, 50, 100, 200, bp of any other capture probe that hybridizes to the target genetic locus in a tagged DNA clone library, including all intervening distances.

In some embodiments, the method can be performed using two capture probe modules per target genetic locus, wherein one hybridizes to the "Watson" strand (non-coding or template strand) upstream of the target region and one hybridizes to the "Crick" strand (coding or non-template strand) downstream of the target region.

In particular embodiments, the methods contemplated herein can further be performed multiple times with any number of capture probe modules, for example 2, 3, 4, 5, 6, 7, 8, 9, or 10 or more capture probe modules per target genetic locus any number of which hybridize to the Watson or Crick strand in any combination. In some embodiments, the sequences obtained can be aligned to one another in order to identify any of a number of differences.

In certain embodiments, a plurality of target genetic loci are interrogated, e.g., 100, 200, 300, 400, 500, 600, 700, 800, 900, 1000, 1500, 2000, 2500, 3000, 3500, 4000, 4500, 5000, 10000, 50000, 100000, 500000 or more in a single reaction, using one or more capture probe modules.

(b) Sequencing

In particular embodiments, the quantitative genetic analysis comprises sequencing a plurality of hybrid nucleic acid molecules, as discussed elsewhere herein, supra, to generate sufficient sequencing depths to obtain a plurality of unique sequencing reads. A unique read is defined as the single consensus read from a "family" of reads that all share the same read code and sequence start point within DNA. Each capture probe yields a set of unique reads that are computationally distilled from total reads by grouping into families. The unique reads for a given sample are then computed as the average of all the unique reads observed on a probe-by-probe basis. Cases where there is an obvious copy number change are excluded from the data set used to compute the average. Unique reads are important because each unique read must be derived from a unique DNA clone. Each unique read represents the input and analysis of a haploid equivalent of genomic DNA. The sum of unique reads is the sum of haploid genomes analyzed. The number of genomes analyzed, in turn, defines the sensitivity of the sequencing assay. By way of a non-limiting example, if the average unique read count is 100 genome equivalents, then that particular assay has a sensitivity of being able to detect one mutant read in 100, or 1%. Any observation less than this is not defensible.

In particular embodiments, the quantitative genetic analysis comprises multiplex sequencing of hybrid nucleic acid molecules derived from a plurality of samples.

In various embodiments, the quantitative genetic analysis comprises obtaining one or more or a plurality of tagged DNA library clones, each clone comprising a first DNA sequence and a second DNA sequence, wherein the first DNA sequence comprises a sequence in a targeted genetic locus and the second DNA sequence comprises a capture probe sequence; performing a paired end sequencing reaction on the one or more clones and obtaining one or more sequencing reads or performing a sequencing reaction on the one or more clones in which a single long sequencing read of greater than about 100, 200, 300, 400, 500 or more nucleotides is obtained, wherein the read is sufficient to identify both the first DNA sequence and the second DNA sequence; and ordering or clustering the sequencing reads of the one or more clones according to the probe sequences of the sequencing reads.

(c) Bioinformatics Analysis

In various embodiments, the quantitative genetic analysis further comprises bioinformatic analysis of the sequencing reads. Bioinformatic analysis excludes any purely mental analysis performed in the absence of a composition or method for sequencing. In certain embodiments, bioinformatics analysis includes, but is not limited to: sequence alignments; genome equivalents analysis; single nucleotide variant (SNV) analysis; gene copy number variation (CNV) analysis; and detection of genetic lesions. In particular embodiments, bioinformatics analysis is useful to quantify the number of genome equivalents analyzed in the DNA clone library; to detect the genetic state of a target genetic locus; to detect genetic lesions in a target genetic locus; and to measure copy number fluctuations within a target genetic locus.

Sequence alignments may be performed between the sequence reads and one or more human reference DNA sequences. In particular embodiments, sequencing alignments can be used to detect genetic lesions in a target genetic locus including, but not limited to detection of a nucleotide transition or transversion, a nucleotide insertion or deletion, a genomic rearrangement, a change in copy number, or a gene fusion. Detection of genetic lesions that are causal or prognostic indicators may be useful in the diagnosis, prognosis, treatment, and/or monitoring of a particular genetic condition or disease.

Also contemplated herein, are methods for sequence alignment analysis that can be performed without the need for alignment to a reference sequence, referred to herein as horizontal sequence analysis. Such analysis can be performed on any sequences generated by the methods contemplated herein or any other methods. In particular embodiments, the sequence analysis comprises performing sequence alignments on the reads obtained by the methods contemplated herein.

In one embodiment, the genome equivalents in a DNA clone library are determined using bioinformatics-based counting after sequencing is performed. Each sequencing read is associated with a particular capture probe, and the collection of reads assigned to each capture probe is parsed into groups. Within a group, sets of individual reads share the same read code and the same DNA sequence start position within genomic sequence. These individual reads are grouped into a "family" and a single consensus representative of this family is carried forward as a "unique read." All of the individual reads that constituted a family are derived from a single ligation event and thus, they are amplification-derived "siblings" of one another. Each unique read is considered a unique ligation event and the sum of unique reads is considered equivalent to the number of genome equivalents analyzed.

As the number of unique clones approaches the total number of possible sequence combinations, probability dictates that the same code and start site combinations will be created by independent events and that these independent events will be inappropriately grouped within single families. The net result will be an underestimate of genome equivalents analyzed, and rare mutant reads may be discarded as sequencing errors because they overlap with wild-type reads bearing the same identifiers.

In particular embodiments, to provide an accurate analysis for DNA clone libraries, the number of genome equivalents analyzed is about 1/10, about 1/12, about 1/14, about 1/16, about 1/18, about 1/20, about 1/25 or less the number of possible unique clones. It should be understood that the procedure outlined above is merely illustrative and not limiting.

In some embodiments, the number of genome equivalents to be analyzed may need to be increased. To expand the depth of genome equivalents, at least two solutions are contemplated. The first solution is to use more than one adaptor set per sample. By combining adaptors, it is possible to multiplicatively expand the total number of possible clones and therefore, expand the comfortable limits of genomic input. The second solution is to expand the read code by 1, 2, 3, 4, or 5 or more bases. The number of possible read codes that differ by at least 2 bases from every other read code scales as $4^{(n-1)}$ where n is the number of bases within a read code. Thus, in a non-limiting example, if a read code is 5 nucleotides and $4^{(5-1)}=256$; therefore, the inclusion of additional bases expands the available repertoire by a factor of four for each additional base.

In one embodiment, quantitative genetic analysis comprises bioinformatic analysis of sequencing reads to identify rare single nucleotide variants (SNV).

Next-generation sequencing has an inherent error rate of roughly 0.02-0.02%, meaning that anywhere from 1/200 to 1/500 base calls are incorrect. To detect variants and other mutations that occur at frequencies lower than this, for example at frequencies of 1 per 1000 sequences, it is necessary to invoke molecular annotation strategies. By way of a non-limiting example, analysis of 5000 unique molecules using targeted sequence capture technology would generate—at sufficient sequencing depths of >50,000 reads—a collection of 5000 unique reads, with each unique read belonging to a "family" of reads that all possess the same read code. A SNV that occurs within a family is a candidate for being a rare variant. When this same variant is observed in more than one family, it becomes a very strong candidate for being a rare variant that exists within the starting sample. In contrast, variants that occur sporadically within families are likely to be sequencing errors and variants that occur within one and only one family are either rare or the result of a base alteration that occurred ex vivo (e.g., oxidation of a DNA base or PCR-introduced errors).

In one embodiment, the methods of detecting SNVs comprise introducing 10-fold more genomic input (genomes or genome equivalents) as the desired target sensitivity of the assay. In one non-limiting example, if the desired sensitivity is 2% (2 in 100), then the experimental target is an input of 2000 genomes.

In particular embodiments, bioinformatics analysis of sequencing data is used to detect or identify SNV associated with a genetic state, condition or disease, genetic mosaicism, fetal testing, paternity testing, predicting response to drug treatment, diagnosing or monitoring a medical condition, microbiome profiling, pathogen screening, and monitoring organ transplants.

In various embodiments, a method for copy number determination analysis is provided comprising obtaining one or more or a plurality of clones, each clone comprising a first DNA sequence and a second DNA sequence, wherein the first DNA sequence comprises a sequence in a targeted genetic locus and the second DNA sequence comprises a capture probe sequence. In related embodiments, a paired end sequencing reaction on the one or more clones is performed and one or more sequencing reads are obtained. In another embodiment, a sequencing reaction on the one or more clones is performed in which a single long sequencing read of greater than about 100 nucleotides is obtained, wherein the read is sufficient to identify both the first DNA sequence and the second DNA sequence. The sequencing reads of the one or more clones can be ordered or clustered according to the probe sequence of the sequencing reads.

Copy number analyses include, but are not limited to analyses, that examine the number of copies of a particular gene or mutation that occurs in a given genomic DNA sample and can further include quantitative determination of the number of copies of a given gene or sequence differences in a given sample. In particular embodiments, copy number analysis is used to detect or identify gene amplification associated with genetic states, conditions, or diseases, fetal testing, genetic mosaicism, paternity testing, predicting response to drug treatment, diagnosing or monitoring a medical condition, microbiome profiling, pathogen screening, and monitoring organ transplants.

In particular embodiments, bioinformatics analysis of sequencing data is used to detect or identify one or more sequences or genetic lesions in a target locus including, but not limited to detection of a nucleotide transition or transversion, a nucleotide insertion or deletion, a genomic rearrangement, a change in copy number, or a gene fusion. Detection of genetic lesions that are causal or prognostic indicators may be useful in the diagnosis, prognosis, treatment, and/or monitoring of a particular genetic condition or disease. In one embodiment, genetic lesions are associated with genetic states, conditions, or diseases, fetal testing, genetic mosaicism, paternity testing, predicting response to drug treatment, diagnosing or monitoring a medical condition, microbiome profiling, pathogen screening, and monitoring organ transplants.

F. Clinical Applications of Quantitative Genetic Analysis

In various embodiments, the present invention contemplates a method of detecting, identifying, predicting, diagnosing, or monitoring a condition or disease in a subject.

In particular embodiments, a method of detecting, identifying, predicting, diagnosing, or monitoring a genetic state, condition or disease in a subject comprises performing a quantitative genetic analysis of one or more target genetic loci in a DNA clone library to detect or identify a change in the sequence at the one or more target genetic loci. In one embodiment, the DNA is cfDNA.

In particular embodiments, a method of detecting, identifying, predicting, diagnosing, or monitoring a genetic state, or genetic condition or disease selected from the group consisting of: genetic diseases; genetic mosaicism; fetal testing; paternity testing; paternity testing; predicting response to drug treatment; diagnosing or monitoring a medical condition; microbiome profiling; pathogen screening; and organ transplant monitoring comprises performing a quantitative genetic analysis of one or more target genetic loci in a DNA clone library to detect or identify a nucleotide transition or transversion, a nucleotide insertion or deletion, a genomic rearrangement, a change in copy number, or a gene fusion in the sequence at the one or more target genetic loci.

Illustrative examples of genetic diseases that can be detected, identified, predicted, diagnosed, or monitored with the compositions and methods contemplated herein include, but are not limited to cancer, Alzheimer's disease (APOE1), Charcot-Marie-Tooth disease, Leber hereditary optic neuropathy (LHON), Angelman syndrome (UBE3A, ubiquitin-protein ligase E3A), Prader-Willi syndrome (region in chromosome 15), β-Thalassaemia (HBB, β-Globin), Gaucher disease (type I) (GBA, Glucocerebrosidase), Cystic fibrosis (CFTR Epithelial chloride channel), Sickle cell disease (HBB, β-Globin), Tay-Sachs disease (HEXA, Hexosaminidase A), Phenylketonuria (PAH, Phenylalanine hydrolyase), Familial hypercholesterolaemia (LDLR, Low density lipoprotein receptor), Adult polycystic kidney disease (PKD1, Polycystin), Huntington disease (HDD, Huntingtin), Neurofibromatosis type I (NF1, NF1 tumour suppressor gene), Myotonic dystrophy (DM, Myotonin), Tuberous sclerosis (TSC1, Tuberin), Achondroplasia (FGFR3, Fibroblast growth factor receptor), Fragile X syndrome (FMR1, RNA-binding protein), Duchenne muscular dystrophy (DMD, Dystrophin), Haemophilia A (F8C, Blood coagulation factor VIII), Lesch-Nyhan syndrome (HPRT1, Hypoxanthine guanine ribosyltransferase 1), and Adrenoleukodystrophy (ABCD1).

Illustrative examples of cancers that can be detected, identified, predicted, diagnosed, or monitored with the compositions and methods contemplated herein include, but are not limited to: B cell cancer, e.g., multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angioarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In one embodiment, the genetic lesion is a lesion annotated in the Cosmic database (the lesions and sequence data can be downloaded from cancer.sanger.ac.uk/cosmic/census) or a lesion annotated in the Cancer Genome Atlas (the lesions and sequence data can be downloaded from tcga-data.nci.nih.gov/tcga/tcgaDownload.jsp).

Illustrative examples of genes that harbor one or more genetic lesions associated with cancer that can be detected, identified, predicted, diagnosed, or monitored with the compositions and methods contemplated herein include, but are not limited to ABCB1, ABCC2, ABCC4, ABCG2, ABL1, ABL2, AKT1, AKT2, AKT3, ALDH4A1, ALK, APC, AR, ARAF, ARFRP1, ARID1A, ATM, ATR, AURKA, AURKB, BCL2, BCL2A1, BCL2L1, BCL2L2, BCL6, BRAF, BRCA1, BRCA2, C1orf144, CARD11, CBL, CCND1, CCND2, CCND3, CCNE1, CDH1, CDH2, CDH20, CDH5, CDK4, CDK6, CDK8, CDKN2A, CDKN2B, CDKN2C, CEBPA, CHEK1, CHEK2, CRKL, CRLF2, CTNNB1, CYP1B1, CYP2C19, CYP2C8, CYP2D6, CYP3A4, CYP3A5, DNMT3A, DOT1L, DPYD, EGFR, EPHA3, EPHA5, EPHA6, EPHA7, EPHB1, EPHB4, EPHB6, EPHX1, ERBB2, ERBB3, ERBB4, ERCC2, ERG, ESR1, ESR2, ETV1, ETV4, ETV5, ETV6, EWSR1, EZH2, FANCA, FBXW7, FCGR3A, FGFR1, FGFR2, FGFR3, FGFR4, FLT1, FLT3, FLT4, FOXP4, GATA1, GNA11, GNAQ, GNAS, GPR124, GSTP1, GUCY1A2, HOXA3, HRAS, HSP9OAA1, IDH1, IDH2, IGF1R, IGF2R, IKBKE, IKZF1, INHBA, IRS2, ITPA, JAK1, JAK2, JAK3, JUN, KDR, KIT, KRAS, LRP1B, LRP2, LTK, MAN1B1, MAP2K1, MAP2K2, MAP2K4, MCL1, MDM2, MDM4, MEN1, MET, MITF, MLH1, MLL, MPL, MRE11A, MSH2, MSH6, MTHFR, MTOR, MUTYH, MYC, MYCL1, MYCN, NF1, NF2, NKX2-1, NOTCH1, NPM1, NQO1, NRAS, NRP2, NTRK1, NTRK3, PAK3, PAX5, PDGFRA, PDGFRB, PIK3CA, PIK3R1, PKHD1, PLCG1, PRKDC, PTCH1, PTEN, PTPN11, PTPRD, RAF1, RARA, RB1, RET, RICTOR, RPTOR, RUNX1, SLC19A1, SLC22A2, SLCO1B3, SMAD2, SMAD3, SMAD4, SMARCA4, SMARCB1, SMO, SOD2, SOX10, SOX2, SRC, STK11, SULT1A1, TBX22, TET2, TGFBR2, TMPRSS2, TNFRSF14, TOP1, TP53, TPMT, TSC1, TSC2, TYMS, UGT1A1, UMPS, USP9X, VHL, and WT1.

In particular embodiments, the genetic lesion comprises a nucleotide transition or transversion, a nucleotide insertion or deletion, a genomic rearrangement, a change in copy number, or a gene fusion.

In one embodiment, the genetic lesion is a gene fusion that fuses the 3' coding region of the ALK gene to another gene.

In one embodiment, the genetic lesion is a gene fusion that fuses the 3' coding region of the ALK gene to the EML4 gene.

Illustrative examples of conditions suitable for fetal testing that can be detected, identified, predicted, diagnosed, or monitored with the compositions and methods contemplated herein include but are not limited to: Down Syndrome (Trisomy 21), Edwards Syndrome (Trisomy 18), Patau Syndrome (Trisomy 13), Klinefelter's Syndrome (XXY), Triple X syndrome, XYY syndrome, Trisomy 8, Trisomy 16, Turner Syndrome (XO), Robertsonian translocation, DiGeorge Syndrome and Wolf-Hirschhorn Syndrome.

Illustrative examples of alleles suitable for paternity testing that can be detected, identified, predicted, diagnosed, or monitored with the compositions and methods contemplated herein include but are not limited to 16 or more of: D20S1082, D6S474, D12ATA63, D22S1045, D1051248, D151677, D11S4463, D4S2364, D9S1122, D2S1776, D10S1425, D3S3053, D5S2500, D1S1627, D3S4529, D2S441, D17S974, D6S1017, D4S2408, D9S2157, Amelogenin, D17S1301, D1GATA113, D18S853, D20S482, and D14S1434.

Illustrative examples of genes suitable for predicting the response to drug treatment that can be detected, identified, predicted, diagnosed, or monitored with the compositions and methods contemplated herein include, but are not limited to, one or more of the following genes: ABCB1 (ATP-binding cassette, sub-family B (MDR/TAP), member 1), ACE (angiotensin I converting enzyme), ADH1A (alcohol dehydrogenase 1A (class I), alpha polypeptide), ADH1B (alcohol dehydrogenase D3 (class I), beta polypeptide), ADH1C (alcohol dehydrogenase 1C (class I), gamma polypeptide), ADRB1 (adrenergic, beta-1-, receptor), ADRB2 (adrenergic, beta-2-, receptor, surface), AHR (aryl hydrocarbon receptor), ALDH1A1 (aldehyde dehydrogenase 1 family, member A1), ALOX5 (arachidonate 5-lipoxygenase), BRCA1 (breast cancer 1, early onset), COMT (catechol-O-methyltransferase), CYP2A6 (cytochrome P450, family 2, subfamily A, polypeptide 6), CYP2B6 (cytochrome P450, family 2, subfamily B, polypeptide 6), CYP2C9 (cytochrome P450, family 2, subfamily C, polypeptide 9), CYP2C19 (cytochrome P450, family 2, subfamily C, polypeptide 19), CYP2D6 (cytochrome P450, family 2, subfamily D, polypeptide 6), CYP2J2 (cytochrome P450, family 2, subfamily J, polypeptide 2), CYP3A4 (cytochrome P450, family 3, subfamily A, polypeptide 4), CYP3A5 (cytochrome P450, family 3, subfamily A, polypeptide 5), DPYD (dihydropyrimidine dehydrogenase), DRD2 (dopamine receptor D2), F5 (coagulation factor V), GSTP1 (glutathione S-transferase pi), HMGCR (3-hydroxy-3-methylglutaryl-Coenzyme A reductase), KCNH2 (potassium voltage-gated channel, subfamily H (eag-related), member 2), KCNJ11 (potassium inwardly-rectifying channel, subfamily J, member 11), MTHFR (5,10-methylenetetrahydrofolate reductase (NADPH)), NQO1 (NAD(P)H dehydrogenase, quinone 1), P2RY1 (purinergic receptor P2Y, G-protein coupled, 1), P2RY12 (purinergic receptor P2Y, G-protein coupled, 12), PTGIS (prostaglandin 12 (prostacyclin) synthase), SCN5A (sodium channel, voltage-gated, type V, alpha (long QT syndrome 3)), SLC19A1 (solute carrier family 19 (folate transporter), member 1), SLCO1B1 (solute carrier organic anion transporter family, member 1B1), SULT1A1 (sulfotransferase family, cytosolic, 1A, phenol-preferring, member 1), TPMT (thiopurine S-methyltransferase), TYMS (thymidylate synthetase), UGT1A1 (UDP glucuronosyltransferase 1 family, polypeptide A1), VDR (vitamin D (1,25-dihydroxyvitamin D3) receptor), VKORC1 (vitamin K epoxide reductase complex, subunit 1).

Illustrative examples of medical conditions that can be detected, identified, predicted, diagnosed, or monitored with the compositions and methods contemplated herein include, but are not limited to: stroke, transient ischemic attack, traumatic brain injury, heart disease, heart attack, angina, atherosclerosis, and high blood pressure.

Illustrative examples of pathogens that can be screened for with the compositions and methods contemplated herein include, but are not limited to: bacteria fungi, and viruses.

Illustrative examples of bacterial species that can be screened for with the compositions and methods contemplated herein include, but are not limited to: a *Mycobacterium* spp., a *Pneumococcus* spp., an *Escherichia* spp., a *Campylobacter* spp., a *Corynebacterium* spp., a *Clostridium* spp., a *Streptococcus* spp., a *Staphylococcus* spp., a *Pseudomonas* spp., a *Shigella* spp., a *Treponema* spp., or a *Salmonella* spp.

Illustrative examples of fungal species that can be screened for with the compositions and methods contemplated herein include, but are not limited to: an *Aspergillis* spp., a *Blastomyces* spp., a *Candida* spp., a *Coccicioides* spp., a *Cryptococcus* spp., dermatophytes, a *Tinea* spp., a *Trichophyton* spp., a *Microsporum* spp., a *Fusarium* spp., a *Histoplasma* spp., a *Mucoromycotina* spp., a *Pneumocystis* spp., a *Sporothrix* spp., an *Exserophilum* spp., or a *Cladosporium* spp.

Illustrative examples of viruses that can be screened for with the compositions and methods contemplated herein include, but are not limited to: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV), HIV (human immunodeficiency virus; including HIV type 1, and HIV type 2), visna-maedi virus (VMV) virus, the caprine arthritis-encephalitis virus (CAEV), equine infectious anemia virus (EIAV), feline immunodeficiency virus (Hy), bovine immune deficiency virus (BIV), and simian immunodeficiency virus (SIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, and any encephaliltis causing virus.

Illustrative examples of genes suitable for monitoring an organ transplant in a transplant recipient that can be detected, identified, predicted, diagnosed, or monitored with the compositions and methods contemplated herein include, but are not limited to, one or more of the following genes: HLA-A, HLA-B, HLA-C, HLA-DR, HLA-DP, and HLA-DQ.

In particular embodiments, a bioinformatic analysis is used to quantify the number of genome equivalents analyzed in the DNA clone library; detect genetic variants in a target genetic locus; detect mutations within a target genetic locus; detect genetic fusions within a target genetic locus; or measure copy number fluctuations within a target genetic locus.

G. Companion Diagnostics

In various embodiments, a companion diagnostic for a genetic disease is provided, comprising: isolating or obtaining DNA, e.g., cfDNA from a biological sample of a subject; removing the terminal phosphate residues of the DNA; treating the dephosphorylated DNA with one or more end-repair enzymes to generate end-repaired DNA; ligating one or more double-stranded DNA (dsDNA) pre-adaptors to the 3' end of each strand of the end-repaired DNA to form pre-adaptor/end-repaired DNA complexes, wherein each dsDNA pre-adaptor comprises a ligation strand oligonucleotide that is ligated to the 3' end of each strand of the end-repaired DNA, and a non-ligation partner strand oligonucleotide; displacing the non-ligation partner strand oligonucleotide from the pre-adaptor/end-repaired DNA complexes with a repair oligonucleotide, to form adaptor/end-repaired DNA complexes, wherein each adaptor comprises the ligation strand oligonucleotide and the repair oligonucleotide; and treating the adaptor/end-repaired DNA complexes with one or more enzymes to form a contiguous, double-stranded, DNA library; amplifying the DNA library to generate a DNA clone library; determining the number of genome equivalents in the DNA clone library; and performing a quantitative genetic analysis of one or more biomarkers associated with the genetic disease in the DNA clone library, wherein detection of, or failure to detect, at least one of the one or more biomarkers indicates whether the subject should be treated for the genetic disease.

As used herein, the term "companion diagnostic" refers to a diagnostic test that is linked to a particular anti-cancer therapy. In a particular embodiment, the diagnostic methods comprise detection of genetic lesion in a biomarker associated with in a biological sample, thereby allowing for prompt identification of patients should or should not be treated with the anti-cancer therapy.

Anti-cancer therapy includes, but is not limited to surgery, radiation, chemotherapeutics, anti-cancer drugs, and immunomodulators.

Illustrative examples of anti-cancer drugs include, but are not limited to: alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin and its pegylated formulations, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethyl amine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; aminopterin; xeloda; ibandronate; CPT-11; topoisomerase inhibitor RFS 2000; difluoromethylornithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Illustrative examples of immunomodulators include, but are not limited to: cyclosporine, tacrolimus, tresperimus, pimecrolimus, sirolimus, verolimus, laflunimus, laquinimod and imiquimod, as well as analogs, derivatives, salts, ions and complexes thereof.

All publications, patent applications, and issued patents cited in this specification are herein incorporated by reference as if each individual publication, patent application, or issued patent were specifically and individually indicated to be incorporated by reference. U.S. patent application Ser. No. 14/102,285, filed Dec. 10, 2013, and Ser. No. 14/466,741, filed Aug. 22, 2014, are each incorporated by reference herein, in its entirety.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1: Proof of Principle for High Efficiency Adaptor Ligation

Figure 2:
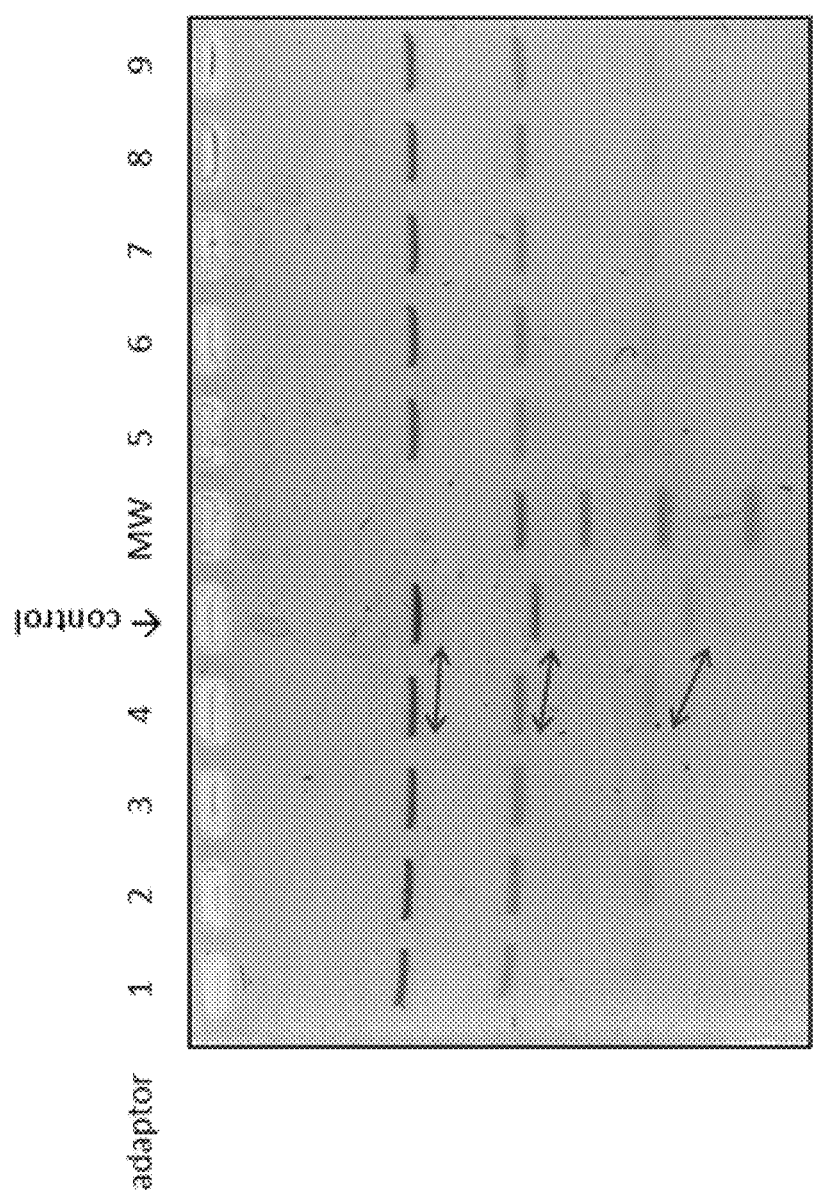
FIG. 2 shows a representative image of an agarose gel of the complete ligation of RsaI digested, dephosphorylated pUC19 plasmid to a series of nine different HE adaptors. Unligated fragments are indicated in the control lane, which is next to the molecular weight (MW) markers of 740, 500, 300, and 150 bp (top to bottom). The complete shift in the mobility of the three vector fragments (arrows) indicates the complete ligation of adaptors to both ends across all nine adaptors. These results show that the HE ligation technology is generalizable.

This example provides direct quantitatively evidence that the high efficiency ligation strategies contemplated herein result in ligation to both ends of the DNA fragment in the absence of adaptor dimer formation (FIG. 2).

Plasmid DNA from the cloning vector pUC19 was digested with the restriction enzyme RsaI to generate blunt ends and dephosphorylated with Antarctic Alkaline Phosphatase. These blunt-ended, dephosphorylated DNA fragments were ligated to a collection of nine different high-efficiency adaptors (Table 1). In all cases, a quantitative shift in fragment mobility was observed following the ligation reaction (arrows), and the shift in mobility was equivalent to the attachment of an adaptor to each end of each DNA fragment. This example provides a proof of principle that the compositions and methods contemplated herein result in high efficiency ligation of adapters to DNA fragments, thereby increasing the overall efficiency of constructing DNA libraries.

Example 2: High Efficiency DNA Library Construction

I. Fragment End Repair

Cell-free DNA (cfDNA) fragment ends were dephosphorylated, internal damage to the DNA duplex was repaired and DNA termini was "polished" to blunt-ends. The resulting fragments are referred to as "end-repaired fragments."

The cfDNA fragment ends were dephosphorylated by combining 81 µl of purified cfDNA, 10 µl of New England Biolabs (NEB) CutSmart buffer (B7204S), and 5 µl of NEB Shrimp Alkaline Phosphatase (M0371). The reaction mixture was incubated at 37° C. for 15 min. and then at 65° C. for 5 min.

The internal damage to dephosphorylated cfDNA fragments was repaired by adding 4 µl of the following mixture, prepared on ice: 1.1 µl of 10 mM dNTP mix (NEB N0447), 2.2 µl of PreCR enzyme mix (M0309) and 1.1 µl of T4 DNA polymerase (M0203). This reaction mixture was incubated at 20° C. for 15 min. and then at 70° C. for 10 min. cfDNA fragments repaired and polished in this manner are ready for direct use in a DNA ligation reaction.

II. Pre-Adaptor Design

Several design considerations were used to generate the pre-adaptors, which are made up of a ligation strand oligonucleotide and a complementary partner strand oligonucleotide with a blocked 3' end.

The pre-adaptors used in this example were designed to have the following features: a ligation strand oligonucleotide that is 10 nt in length; an equal balance of A/T or G/C residues; each of the four DNA bases represented at each base position within each set of pre-adaptors; a predicted melting temperature of the 10 base sequence that is ~37° C. in 50 mM Na$^+$ (or K$^+$), 10 mM MgCl$_2$; both an A/T and a G/C nt as the first two bases of each pre-adaptor sequence; a complementary partner oligonucleotide sequence that is 8

TABLE 1

Ligation strand and partner strand oligonucleotide sequences used to create test he adaptors

| Adaptor ID | Ligation strand (5'phosphate, 5' to 3') | SEQ ID: | Partner strand (5' to 3', 3' ddC) | SEQ ID: |
|---|---|---|---|---|
| 1 | GAGGGTCTACCTTCTTNNNNNNTGTATT CGAATTCTCTGGTCCTGCA | 1 | AAGGTAGACCCT | 10 |
| 2 | GCTCTAGACGTCATCGNNNNNNTGTATT CGAATTCTCTGGTCCTGCA | 2 | TGACGTCTAGAG | 11 |
| 3 | GGATACTCGTAGCGGCNNNNNNTGTATT CGAATTCTCTGGTCCTGCA | 3 | GCTACGAGTATC | 12 |
| 4 | GTCACGAGTAGAGAAANNNNNNTGTATT CGAATTCTCTGGTCCTGCA | 4 | CTCTACTCGTGA | 13 |
| 5 | GAGGGTCTACCTTAGTNNNNNNTGTATT CGAATTCTCTGGTCCTGCA | 5 | AAGGTAGACCCT | 14 |
| 6 | GCTCTAGACGTCAGAGNNNNNNTGTATT CGAATTCTCTGGTCCTGCA | 6 | TGACGTCTAGAG | 15 |
| 7 | GGATACTCGTAGCTTCNNNNNNTGTATT CGAATTCTCTGGTCCTGCA | 7 | GCTACGAGTATC | 16 |
| 8 | GTCACGAGTAGAGCCANNNNNNTGTATT CGAATTCTCTGGTCCTGCA | 8 | CTCTACTCGTGA | 17 |
| 9 | GAGGGTCTACCTTGCTNNNNNNTGTATT CGAATTCTCTGGTCCTGCA | 9 | AAGGTAGACCCT | 18 | nt in length, that is chemically blocked with by using 2-hydroxyl ribose-modified DNA bases (MWG Eurofins), and that has a melting temperature of ~25° C. in 50 mM Na$^+$ or K$^+$, 10 mM MgCl$_2$.

Even with design constrains in place, empirical performance screening of adaptor sets was performed. In the current experiment, five sets of four adaptors having acceptable performance were identified (see, e.g., Table 2). The column labeled "score" shows the percent cloning efficiency of each adaptor relative to the best performing adaptor (set 6-2).

a final volume of 50 μl. The reaction was mixed and incubated at 20° C. for 60 min., then at 65° C. for 10 min, then cooled to room temperature.

After the ligation reaction, 50 ul of TEzero (10 mM Tris pH 8.0, 0.1 mM EDTA, 0.05% Tween 20). and 120 ul of DNA purification beads were added to each reaction and mixed well. The reaction was incubated for 10 min. at room temperature, then the beads were washed two times with 200 μl of 70% ethanol/water (v/v), air-dried briefly (~5 min.), and eluted with 20 μl of TEzero.

TABLE 2

Empirically validated adaptor sets.

| Ligation strand oligonucleotides | | SEQ ID | Partner strand oligonucleotides | | Score |
|---|---|---|---|---|---|
| Name | Sequence | | Name | Sequence | |
| he_lig_5-1 | /5Phos/CTGAGCTAGT | 19 | he_part_5-1 | TAGCTCA[3-dG-Q] | 60 |
| he_lig_5-2 | /5Phos/GACTCGATAG | 20 | he_part_5-2 | ATCGAGT[3-dC-Q] | 97 |
| he_lig_5-3 | /5Phos/TCAGATCGTC | 21 | he_part_5-3 | CGATCTG[3-dA-Q] | 27 |
| he_lig_5-4 | /5Phos/AGTCTAGCCA | 22 | he_part_5-4 | GCTAGAC[3-dT-Q] | 84 |
| he_lig_6-1 | /5Phos/GGATTACCCT | 23 | he_part_6-1 | GGTAATC[3-dC-Q] | 70 |
| he_lig_6-2 | /5Phos/CTTACGGATG | 24 | he_part_6-2 | TCCGTAA[3-dG-Q] | 100 |
| he_lig_6-3 | /5Phos/ACCGATTGAC | 25 | he_part_6-3 | CAATCGG[3-dT-Q] | 74 |
| he_lig_6-4 | /5Phos/TAGCGCATGA | 26 | he_part_6-4 | ATGCGCT[3-dA-Q] | 48 |
| he_lig_8-1 | /5Phos/ATGTCCAGCT | 27 | he_part_8-1 | CTGGACA[3-dT-Q] | 24 |
| he_lig_8-2 | /5Phos/CACAGGTTAG | 28 | he_part_8-2 | AACCTGT[3-dG-Q] | 46 |
| he_lig_8- | /5Phos/TGACATGCTC | 29 | he_part_8-3 | GCATGTC[3-dA-Q] | 53 |
| he_lig_8-4 | /5Phos/GCTGTACAGA | 30 | he_part_8-4 | TGTACAG[3-dC-Q] | 48 |
| he_lig_11-1 | /5Phos/TCAAGTCGGT | 31 | he_part_11-1 | CGACTTG[3-dA-Q] | 83 |
| he_lig_11-2 | /5Phos/GTTCAGACTG | 32 | he_part_11-2 | GTCTGAA[3-dC-Q] | 95 |
| he_lig_11-3 | /5Phos/CAGGTCTAAC | 33 | he_part_11-3 | TAGACCT[3-dG-Q] | 33 |
| he_lig_11-4 | /5Phos/AGCTCAGTCA | 34 | he_part_11-4 | ACTGAGC[3-dT-Q] | 98 |
| he_lig_12-1 | /5Phos/GATCCGTACT | 35 | he_part_12-1 | TACGGAT[3-dC-Q] | 91 |
| he_lig_12-2 | /5Phos/ACAGTCGTAG | 36 | he_part_12-2 | ACGACTG[3-dT-Q] | 98 |
| he_lig_12-3 | /5Phos/TGGTAACCTC | 37 | he_part_12-3 | GGTTACC[3-dA-Q] | 85 |
| he_lig_12-4 | /5Phos/CTCAGTAGGA | 38 | he_part_12-4 | CTACTGA[3-dG-Q] | 93 |

III. Ligation of Pre-Adaptors

A pre-adaptor was ligated to end-repaired fragments generated in step I of this example. 25 μl of end-repaired fragment was combined with 10 μl of 10 μM adaptor. Typically, 1 to 4 ligation reactions were performed depending on the number of separate adaptors added to the reaction. 15 μl of ligation cocktail (5 μl of 10× T4-DNA ligation buffer, 7.5 μl of 50% PEG8000, and 2.5 μl of HC T4 DNA ligase (NEB; M0202)) was added to each ligation reaction in IV. Repair Oligonucleotides A complete listing of repair oligonucleotides used in this example is shown in Table 3. Each repair oligonucleotide is a pool of 249 individual oligonucleotides. The invariant sequence in each repair oligonucleotide represents a PCR primer binding site and is shown in Table 3A.

Each of the 249 oligonucleotides comprises a 5 nucleotide sample code, shown as an "XXXXX" in repair oligonucleotide sequence. The 5 nucleotide sample are shown in Table 3B. The 5 nucleotide codes consist of 256 possible unique sequences that were chosen to be 2 base changes different from every other code in the set. This feature enabled unique and distinct reads to be differentiated from reads that appeared to be unique owing to a sequencing error in the code region. Seven codes in which G residues are over-represented and that were shown empirically to interfere with adaptor function were removed, leaving 249 random codes.

TABLE 3A

Repair oligos and their associated read codes: Full length repair oligos (RO) compatible with ligation oligos

| Name | Sequence | SEQ ID NO: |
|---|---|---|
| RO_5-1 | TGCAGGACCAGAGAATTCGAATACAXXXXXACTAGCTCAG | 39 |
| RO_5-2 | TGCAGGACCAGAGAATTCGAATACAXXXXXCTATCGAGTC | 40 |
| RO_5-3 | TGCAGGACCAGAGAATTCGAATACAXXXXXGACGATCTGA | 41 |
| RO_5-4 | TGCAGGACCAGAGAATTCGAATACAXXXXXTGGCTAGACT | 42 |
| RO_6-1 | TGCAGGACCAGAGAATTCGAATACAXXXXXAGGGTAATCC | 43 |
| RO_6-2 | TGCAGGACCAGAGAATTCGAATACAXXXXXCATCCGTAAG | 44 |
| RO_6-3 | TGCAGGACCAGAGAATTCGAATACAXXXXXGTCAATCGGT | 45 |
| RO_6-4 | TGCAGGACCAGAGAATTCGAATACAXXXXXTCATGCGCTA | 46 |
| RO_7-1 | TGCAGGACCAGAGAATTCGAATACAXXXXXACTGCTAGCA | 47 |
| RO_7-2 | TGCAGGACCAGAGAATTCGAATACAXXXXXCAGCGATCAT | 48 |
| RO_7-3 | TGCAGGACCAGAGAATTCGAATACAXXXXXGTCATCGATG | 49 |
| RO_7-4 | TGCAGGACCAGAGAATTCGAATACAXXXXXTGATAGCTGC | 50 |
| RO_8-1 | TGCAGGACCAGAGAATTCGAATACAXXXXXAGCTGGACAT | 51 |
| RO_8-2 | TGCAGGACCAGAGAATTCGAATACAXXXXXCTAACCTGTG | 52 |
| RO_8-3 | TGCAGGACCAGAGAATTCGAATACAXXXXXGAGCATGTCA | 53 |
| RO_8-4 | TGCAGGACCAGAGAATTCGAATACAXXXXXTCTGTACAGC | 54 |
| RO_11-1 | TGCAGGACCAGAGAATTCGAATACAXXXXXACCGACTTGA | 55 |
| RO_11-2 | TGCAGGACCAGAGAATTCGAATACAXXXXXCAGTCTGAAC | 56 |
| RO_11-3 | TGCAGGACCAGAGAATTCGAATACAXXXXXGTTAGACCTG | 57 |
| RO_11-4 | TGCAGGACCAGAGAATTCGAATACAXXXXXTGACTGAGCT | 58 |
| RO_12-1 | TGCAGGACCAGAGAATTCGAATACAXXXXXAGTACGGATC | 59 |
| RO_12-2 | TGCAGGACCAGAGAATTCGAATACAXXXXXCTACGACTGT | 60 |
| RO_12-3 | TGCAGGACCAGAGAATTCGAATACAXXXXXGAGGTTACCA | 61 |
| RO_12-4 | TGCAGGACCAGAGAATTCGAATACAXXXXXTCCTACTGAG | 62 |

TABLE 3B

Repair oligos and their associated read codes: XXXXX - Difference 2 sequence codes

| Seq |
|---|
| CGGGT |
| CGGTG |
| CGTGG |
| GCGGT |
| GCGTG |
| GCTGG |

TABLE 3B-continued

Repair oligos and their associated read codes:
XXXXX - Difference 2 sequence codes

| Seq |
|---|
| GGCGT |
| GGCTG |
| GGGCT |
| GGGTC |
| GGTCG |
| GGTGC |
| GTCGG |
| GTGCG |
| GTGGC |
| TGCGG |
| TGGCG |
| TGGGC |
| AAAGG |
| AAGAG |
| AAGGA |
| ACCGG |
| ACGCG |
| ACGGC |
| AGAAG |
| AGAGA |
| AGCCG |
| AGCGC |
| AGGAA |
| AGGCC |
| AGGTT |
| AGTGT |
| AGTTG |
| ATGGT |
| ATGTG |
| ATTGG |
| CACGG |
| CAGCG |
| CAGGC |
| CCAGG |
| CCGAG |
| CCGGA |
| CGACG |
| CGAGC |
| CGCAG |
| CGCGA |
| CGGAC |
| CGGCA |
| GAAAG |
| GAAGA |
| GACCG |
| GACGC |
| GAGAA |
| GAGCC |
| GAGTT |
| GATGT |
| GATTG |
| GCACG |
| GCAGC |
| GCCAG |
| GCCGA |
| GCGAC |
| GCGCA |
| GGAAA |
| GGACC |
| GGATT |
| GGCAC |
| GGCCA |
| GGTAT |
| GGTTA |
| GTAGT |
| GTATG |
| GTGAT |
| GTGTA |
| GTTAG |
| GTTGA |
| TAGGT |
| TAGTG |
| TATGG |
| TGAGT |
| TGATG |
| TGGAT |

TABLE 3B-continued

Repair oligos and their associated read codes:
XXXXX - Difference 2 sequence codes

| Seq |
|---|
| TGGTA |
| TGTAG |
| TGTGA |
| TTAGG |
| TTGAG |
| TTGGA |
| AACGT |
| AACTG |
| AAGCT |
| AAGTC |
| AATCG |
| AATGC |
| ACAGT |
| ACATG |
| ACGAT |
| ACGTA |
| ACTAG |
| ACTGA |
| AGACT |
| AGATC |
| AGCAT |
| AGCTA |
| AGTAC |
| AGTCA |
| ATACG |
| ATAGC |
| ATCAG |
| ATCGA |
| ATGAC |
| ATGCA |
| CAAGT |
| CAATG |
| CAGAT |
| CAGTA |
| CATAG |
| CATGA |
| CCCGT |
| CCCTG |

TABLE 3B-continued

Repair oligos and their associated read codes:
XXXXX - Difference 2 sequence codes

| Seq |
|---|
| CCGCT |
| CCGTC |
| CCTCG |
| CCTGC |
| CGAAT |
| CGATA |
| CGCCT |
| CGCTC |
| CGTAA |
| CGTCC |
| CGTTT |
| CTAAG |
| CTAGA |
| CTCCG |
| CTCGC |
| CTGAA |
| CTGCC |
| CTGTT |
| CTTGT |
| CTTTG |
| GAACT |
| GAATC |
| GACAT |
| GACTA |
| GATAC |
| GATCA |
| GCAAT |
| GCATA |
| GCCCT |
| GCCTC |
| GCTAA |
| GCTCC |
| GCTTT |
| GTAAC |
| GTACA |
| GTCAA |
| GTCCC |
| GTCTT |

TABLE 3B-continued

Repair oligos and their associated read codes:
XXXXX - Difference 2 sequence codes

| Seq |
|---|
| GTTCT |
| GTTTC |
| TAACG |
| TAAGC |
| TACAG |
| TACGA |
| TAGAC |
| TAGCA |
| TCAAG |
| TCAGA |
| TCCCG |
| TCCGC |
| TCGAA |
| TCGCC |
| TCGTT |
| TCTGT |
| TCTTG |
| TGAAC |
| TGACA |
| TGCAA |
| TGCCC |
| TGCTT |
| TGTCT |
| TGTTC |
| TTCGT |
| TTCTG |
| TTGCT |
| TTGTC |
| TTTCG |
| TTTGC |
| AAAAA |
| AAACC |
| AAATT |
| AACAC |
| AACCA |
| AATAT |
| AATTA |
| ACAAC |

TABLE 3B-continued

Repair oligos and their associated read codes:
XXXXX - Difference 2 sequence codes

| Seq |
|---|
| ACACA |
| ACCAA |
| ACCCC |
| ACCTT |
| ACTCT |
| ACTTC |
| ATAAT |
| ATATA |
| ATCCT |
| ATCTC |
| ATTAA |
| ATTCC |
| ATTTT |
| CAAAC |
| CAACA |
| CACAA |
| CACCC |
| CACTT |
| CATCT |
| CATTC |
| CCAAA |
| CCACC |
| CCATT |
| CCCAC |
| CCCCA |
| CCTAT |
| CCTTA |
| CTACT |
| CTATC |
| CTCAT |
| CTCTA |
| CTTAC |
| CTTCA |
| TAAAT |
| TAATA |
| TACCT |
| TACTC |
| TATAA |

TABLE 3B-continued

Repair oligos and their associated read codes:
XXXXX - Difference 2 sequence codes

| Seq |
|---|
| TATCC |
| TATTT |
| TCACT |
| TCATC |
| TCCAT |
| TCCTA |
| TCTAC |
| TCTCA |
| TTAAA |
| TTACC |
| TTATT |
| TTCAC |
| TTCCA |
| TTTAT |
| TTTTA |

V. Addition of Repair Oligonucleotides to Pre-Adaptor Libraries

Library construction was completed by adding repair oligonucleotides to the adaptor. The repair oligonucleotides illustrated in this example contain a PCR primer binding site; sample codes; and an anchor sequence, which is a random sequence label that acts as a means to identify the sequence, that enables calibration of proper base calls in sequencing reads, and that acts as an anchor for hybridization to the ligation strand oligonucleotide.

4 µl of a 1 µM pool of repair oligonucleotide (see, e.g., Table 3) was added to 20 µl of purified ligation mix from step III of this example.

Next, a 40 µl repair oligonucleotide reaction was prepared by combining 24 µl repair oligonucleotide/ligase mixture with 16 µl of the following mixture, on ice: 11 µl of water, 4.4 µl of buffer "B" (190 µl of CutSmart buffer (NEB; B7204) and 10 µl of 1M dithiothreitol (DTT; Sigma-Aldrich 646563), 1.32 µl of nucleotide mix "N" (combine 50 µl of 10 mM dNTP mixture (NEB; N0447) with 25 µl of 100× NAD+(NEB; B9007) and 0.88 µl of enzyme mix "E" (combine 20 µl of T4 polynucleotide kinase (NEB; M0201), 10 µl of full-length BstI polymerase (NEB; M0328) and 10 µl of Taq DNA ligase (NEB; M0208). The reaction was mixed and incubated at 37° C. for 15 min. then at 60° C. for 15 min.

The reactions were removed from the thermal cycler and 48 ul of bead resuspension solution (19% PEG8000, 2M NaCl, 10 mM Tris pH 8.0, 10 mM EDTA, 0.1% Tween 20) was added to the reaction and incubated at room temperature for 10 min. The beads were washed twice with 200 µl of 70% ethanol, air-dried briefly (~5 min.) and resuspended in 25 µl of TEzero. A magnet was used to localize the beads and the clarified DNA library was transferred to a fresh reaction vessel.

VI. Summary

The resulting DNA libraries constructed using the methods contemplated herein throughout and described in Example 1 are amplification ready and suitable for next generation sequencing, qPCR analysis, and other quantitative genetic analyses of one or more target genetic loci.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for adaptor ligation to one or more DNA fragments comprising:
   (a) removing the terminal phosphate residues of the one or more DNA fragments;
   (b) treating the dephosphorylated DNA fragments with one or more end-repair enzymes to generate end-repaired DNA fragments;
   (c) ligating one or more double-stranded DNA (dsDNA) pre-adaptors to the 3' end of each strand of the end-repaired DNA fragments to form pre-adaptor/end-repaired DNA complexes, wherein each dsDNA pre-adaptor comprises (i) a ligation strand oligonucleotide that is ligated to the 3' end of each strand of the end-repaired DNA fragments and comprises an anchor sequence; and (ii) a non-ligation partner strand oligonucleotide;
   (d) displacing the non-ligation partner strand oligonucleotide from the pre-adaptor/end-repaired DNA complexes with a repair oligonucleotide, wherein the repair oligonucleotide is longer than the ligation strand oligonucleotide, and wherein the 3' end of the repair oligonucleotide is complementary to the 5' end of the ligation strand oligonucleotide;
   (e) ligating the repair oligonucleotide to the 5' end of the end-repaired DNA fragments using a kinase ligase strategy to form adaptor/end-repaired DNA complexes, wherein each adaptor comprises the ligation strand oligonucleotide and the repair oligonucleotide;
   wherein the kinase ligase strategy comprises contacting the adaptor/end repaired DNA complexes with a kinase and a ligase, wherein the kinase adds a phosphate group to the 5' terminal nucleotide of each strand of the end repaired DNA fragments, and wherein the ligase ligates the repair oligonucleotide to the phosphorylated 5' end of each strand of the end repaired DNA fragments; and
   (f) extending the ligation strand oligonucleotide at the 3' end using the repair oligonucleotide as a template to form one or more contiguous dsDNA fragments each comprising an adaptor molecule ligated to each end of the DNA fragment.

2. The method of claim 1, wherein the non-ligation partner strand oligonucleotide comprises a modification at its 3' terminus that prevents ligation to the 5' end of the end-repaired DNA fragments or adaptor dimer formation.

3. The method of claim 1, wherein the source of the one or more DNA fragments is selected from the group consisting of genomic DNA (gDNA), complementary DNA (cDNA), and cell-free DNA (cfDNA).

4. The method of claim 3, wherein the DNA is isolated from a biological sample selected from the group consisting of an amniotic fluid sample, a blood sample, a skin sample, a hair sample, a hair follicle sample, a saliva sample, a mucous sample, a sweat sample, a tear sample, an epithelial tissue sample, a urine sample, a semen sample, a seminal plasma sample, a serum sample, a prostatic fluid sample, a pre-ejaculatory fluid (Cowper's fluid) sample, an ocular fluid sample, an excreta sample, a biopsy sample, an ascites sample, a cerebrospinal fluid sample, a lymph sample, a tissue extract sample, a stool sample, and a formalin-fixed, paraffin embedded (FFPE) sample.

5. The method of claim 1, further comprising repairing damage of the one or more DNA fragments prior to step (c).

6. The method of claim 5, wherein the damage is a deaminated cytosine (Uracil), an abasic site, methylation of guanine to $O^6MeG$, one or more DNA nicks, one or more DNA gaps, or a thymine dimer.

7. The method of claim 1, wherein the ligation strand oligonucleotide further comprises one or more of
   (i) one or more unique read codes;
   (ii) a PCR primer binding site for PCR amplification of the one or more tagged dsDNA fragments;
   (iii) one or more sample codes for sample multiplexing; or
   (iv) one or more primer binding sites for DNA sequencing.

8. The method of claim 1, wherein the repair oligonucleotide comprises an anchor sequence.

9. The method of claim 8, wherein the repair oligonucleotide further comprises one or more of:
   (i) one or more unique read codes;
   (ii) a PCR primer binding site for PCR amplification of the one or more tagged dsDNA fragments;
   (iii) one or more sample codes for sample multiplexing; or
   (iv) one or more primer binding sites for DNA sequencing.

10. The method of claim 1, wherein each of the ligation strand oligonucleotide and the repair oligonucleotide comprise an anchor sequence and wherein the anchor sequence of the ligation strand oligonucleotide is at least partially complementary to the anchor sequence of the repair oligonucleotide.

11. The method of claim 10, wherein each of the ligation strand oligonucleotide and the repair oligonucleotide further comprise a PCR primer binding site for amplification of the one or more tagged dsDNA fragments, wherein the PCR primer binding site of the ligation strand oligonucleotide is complementary to the PCR primer binding site of the repair oligonucleotide.

12. The method of claim 10, wherein each of the ligation strand oligonucleotide and the repair oligonucleotide further comprise a PCR primer binding site for amplification of the one or more tagged dsDNA fragments, and wherein the PCR primer binding site of the ligation strand oligonucleotide is not complementary to the PCR primer binding site of the repair oligonucleotide.

13. The method of claim 12, wherein a primer that binds the PCR primer binding site of the ligation strand oligonucleotide does not substantially bind the PCR primer binding site of the repair oligonucleotide.

14. The method of claim 1, wherein step (c) is performed at a first temperature and step (d) is performed at a second temperature, wherein the second temperature is higher than the first temperature and results in the displacement of the partner strand oligonucleotide from the ligation strand oligonucleotide.

15. The method of claim 14, wherein the first temperature is 22° C. or lower and the second temperature is 37° C. or higher.

16. The method of claim 1, wherein the kinase/ligase strategy of step (e) does not comprise removal of the 5' terminal nucleotide of the end-repaired DNA fragment.

17. The method of claim 1, wherein the ligase used in step (c) is different from the ligase used in step (e).

18. The method of claim 1, wherein the ligase used in step (c) is capable of ligating DNA fragments with blunt ends.

19. The method of claim 1, wherein the ligase used in step (c) is capable of ligating DNA fragments with 5' or 3' overhangs.

20. The method of claim 1, wherein the ligase used in step (c) is a T4 DNA ligase.

21. The method of claim 1, wherein the ligase used in step (e) is a thermo-stable nick-specific ligase.

22. The method of claim 1, wherein the ligase used in step (e) is selected from the list consisting of Taq DNA ligase, *E. coli* DNA ligase, and 9° North ligase.

23. The method of claim 1, wherein the method does not comprise degradation or cleavage of the ligation strand oligonucleotide, the repair oligonucleotide, or the end repaired DNA fragment.

* * * * *

SEQUENCE LISTING

```
<160> NUMBER OF SEQ ID NOS: 62

<210> SEQ ID NO 1
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G

<400> SEQUENCE: 1
gagggtctac cttcttnnnn ntgtattcga attctctggt cctgca            46

<210> SEQ ID NO 2
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G
```

<400> SEQUENCE: 2
gctctagacg tcatcgnnnn ntgtattcga attctctggt cctgca          46

<210> SEQ ID NO 3
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G

<400> SEQUENCE: 3
ggatactcgt agcggcnnnn ntgtattcga attctctggt cctgca          46

<210> SEQ ID NO 4
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G

<400> SEQUENCE: 4
gtcacgagta gagaaannnn ntgtattcga attctctggt cctgca          46

<210> SEQ ID NO 5
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G

<400> SEQUENCE: 5
gagggtctac cttagtnnnn ntgtattcga attctctggt cctgca          46

<210> SEQ ID NO 6
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G

<400> SEQUENCE: 6
gctctagacg tcagagnnnn ntgtattcga attctctggt cctgca          46

<210> SEQ ID NO 7
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G -continued

```
<400> SEQUENCE: 7
ggatactcgt agcttcnnnn ntgtattcga attctctggt cctgca                    46

<210> SEQ ID NO 8
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G

<400> SEQUENCE: 8
gtcacgagta gagccannnn ntgtattcga attctctggt cctgca                    46

<210> SEQ ID NO 9
<211> LENGTH: 46
<212> TYPE: DNA
<213> ORGANISM: Artificial Sequence
<220> FEATURE:
<223> OTHER INFORMATION: Synthesized ligation strand oligonucleotide
<220> FEATURE:
<221> NAME/KEY: misc_feature
<222> LOCATION: (17)..(21)
<223> OTHER INFORMATION: n is A, C, T or G

<400> SEQUENCE: 9
gagggtctac cttgctnnnn ntgtattcga attctctggt cctgca                    46

<210> SEQ ID NO 10
<211> LENGTH: 12
<212> TYPE: DNA
<213> ORGANISM: Artificial Sequence
<220> FEATURE:
<223> OTHER INFORMATION: Synthesized partner strand oligonucleotide

<400> SEQUENCE: 10
aaggtagacc ct                                                         12

<210> SEQ ID NO 11
<211> LENGTH: 12
<212> TYPE: DNA
<213> ORGANISM: Artificial Sequence
<220> FEATURE:
<223> OTHER INFORMATION: Synthesized partner strand oligonucleotide

<400> SEQUENCE: 11
tgacgtctag ag                                                         12

<210> SEQ ID NO 12
<211> LENGTH: 12
<212> TYPE: DNA
<213> ORGANISM: Artificial Sequence
<220> FEATURE:
<223> OTHER INFORMATION: Synthesized partner strand oligonucleotide

<400> SEQUENCE: 12
gctacgagta tc                                                         12

<210> SEQ ID NO 13
<211> LENGTH: 12
<212> TYPE: DNA
<213> ORGANISM: Artificial Sequence
<220> FEATURE:
<223> OTHER INFORMATION: Synthesized partner strand oligonucleotide
```

```
<400> SEQUENCE: 13
ctctactcgt ga                                                              12

<210> SEQ ID NO 14
<211> LENGTH: 12
<212> TYPE: DNA
<213> ORGANISM: Artificial Sequence
<220> FEATURE:
<223> OTHER INFORMATION: Synthesized partner strand oligonucleotide

<400> SEQUENCE: 14
aaggtagacc ct                                                              12

<210> SEQ ID NO 15
<211> LENGTH: 12
<212> TYPE: DNA
<213> ORGANISM: Artificial Sequence
<220> FEATURE:
<223> OTHER INFORMATION: Synthesized partner strand oligonucleotide

<400> SEQUENCE: 15
tgacgtctag ag                                                              12

<210> SEQ ID NO 16
<211> LENGTH: 12
<212> TYPE: DNA
<213> ORGANISM: Artificial Sequence
<220> FEATURE:
<223> OTHER INFORMATION: Synthesized partner strand oligonucleotide

<400> SEQUENCE: 16
gctacgagta tc                                                              12

<210> SEQ ID NO 17
<211> LENGTH: 12
<212> TYPE: DNA
<213> ORGANISM: Artificial Sequence
<220> FEATURE:
<223> OTHER INFORMATION: Synthesized partner strand oligonucleotide

<400> SEQUENCE: 17
ctctactcgt ga                                                              12

<210> SEQ ID NO 18
<211> LENGTH: 12
<212> TYPE: DNA
<213> ORGANISM: Artificial Sequence
<220> FEATURE:
<223> OTHER INFORMATION: Synthesized partner strand oligonucleotide

<400> SEQUENCE: 18
aaggtagacc ct                                                              12

<210> SEQ ID NO 19
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 19
ctgagctagt                                                                 10
```

```
<210> SEQ ID NO 20
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 20
gactcgatag                                                                10

<210> SEQ ID NO 21
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 21
tcagatcgtc                                                                10

<210> SEQ ID NO 22
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 22
agtctagcca                                                                10

<210> SEQ ID NO 23
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 23
ggattaccct                                                                10

<210> SEQ ID NO 24
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 24
cttacggatg                                                                10

<210> SEQ ID NO 25
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 25
accgattgac                                                                10

<210> SEQ ID NO 26
<211> LENGTH: 10
<212> TYPE: DNA
<213> ORGANISM: Artificial Sequence
<220> FEATURE:
<223> OTHER INFORMATION: Synthesized ligation strand oligonucleotide
```

```
<400> SEQUENCE: 26
tagcgcatga                                                              10

<210> SEQ ID NO 27
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 27
atgtccagct                                                              10

<210> SEQ ID NO 28
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 28
cacaggttag                                                              10

<210> SEQ ID NO 29
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 29
tgacatgctc                                                              10

<210> SEQ ID NO 30
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 30
gctgtacaga                                                              10

<210> SEQ ID NO 31
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 31
tcaagtcggt                                                              10

<210> SEQ ID NO 32
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 32
gttcagactg                                                              10
```

```
<210> SEQ ID NO 33
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 33
caggtctaac                                                              10

<210> SEQ ID NO 34
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 34
agctcagtca                                                              10

<210> SEQ ID NO 35
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 35
gatccgtact                                                              10

<210> SEQ ID NO 36
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 36
acagtcgtag                                                              10

<210> SEQ ID NO 37
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 37
tggtaacctc                                                              10

<210> SEQ ID NO 38
<211> LENGTH: 10
<212> TYPE: DNA
<213> ORGANISM: Artificial Sequence
<220> FEATURE:
<223> OTHER INFORMATION: Synthesized ligation strand oligonucleotide

<400> SEQUENCE: 38
ctcagtagga                                                              10

<210> SEQ ID NO 39
<211> LENGTH: 40
<212> TYPE: DNA
<213> ORGANISM: Artificial Sequence
<220> FEATURE:
<223> OTHER INFORMATION: Synthesized repair oligonucleotide
```

<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 39
tgcaggacca gagaattcga atacannnnn actagctcag            40

<210> SEQ ID NO 40
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 40
tgcaggacca gagaattcga atacannnnn ctatcgagtc            40

<210> SEQ ID NO 41
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 41
tgcaggacca gagaattcga atacannnnn gacgatctga            40

<210> SEQ ID NO 42
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 42
tgcaggacca gagaattcga atacannnnn tggctagact            40

<210> SEQ ID NO 43
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 43
tgcaggacca gagaattcga atacannnnn agggtaatcc            40

```
<210> SEQ ID NO 44
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 44
tgcaggacca gagaattcga atacannnnn catccgtaag                                40

<210> SEQ ID NO 45
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 45
tgcaggacca gagaattcga atacannnnn gtcaatcggt                                40

<210> SEQ ID NO 46
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 46
tgcaggacca gagaattcga atacannnnn tcatgcgcta                                40

<210> SEQ ID NO 47
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 47
tgcaggacca gagaattcga atacannnnn actgctagca                                40

<210> SEQ ID NO 48
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3
```

```
<400> SEQUENCE: 48
tgcaggacca gagaattcga atacannnnn cagcgatcat                          40

<210> SEQ ID NO 49
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 49
tgcaggacca gagaattcga atacannnnn gtcatcgatg                          40

<210> SEQ ID NO 50
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 50
tgcaggacca gagaattcga atacannnnn tgatagctgc                          40

<210> SEQ ID NO 51
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 51
tgcaggacca gagaattcga atacannnnn agctggacat                          40

<210> SEQ ID NO 52
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 52
tgcaggacca gagaattcga atacannnnn ctaacctgtg                          40

<210> SEQ ID NO 53
<211> LENGTH: 40
<212> TYPE: DNA
<213> ORGANISM: Artificial Sequence
<220> FEATURE:
<223> OTHER INFORMATION: Synthesized repair oligonucleotide
```

```
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 53
tgcaggacca gagaattcga atacannnnn gagcatgtca                              40

<210> SEQ ID NO 54
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 54
tgcaggacca gagaattcga atacannnnn tctgtacagc                              40

<210> SEQ ID NO 55
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 55
tgcaggacca gagaattcga atacannnnn accgacttga                              40

<210> SEQ ID NO 56
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 56
tgcaggacca gagaattcga atacannnnn cagtctgaac                              40

<210> SEQ ID NO 57
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 57
tgcaggacca gagaattcga atacannnnn gttagacctg                              40
```

```
<210> SEQ ID NO 58
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 58
tgcaggacca gagaattcga atacannnnn tgactgagct                             40

<210> SEQ ID NO 59
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 59
tgcaggacca gagaattcga atacannnnn agtacggatc                             40

<210> SEQ ID NO 60
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 60
tgcaggacca gagaattcga atacannnnn ctacgactgt                             40

<210> SEQ ID NO 61
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3

<400> SEQUENCE: 61
tgcaggacca gagaattcga atacannnnn gaggttacca                             40

<210> SEQ ID NO 62
<211> LENGTH: 40
<212> TYPE: DNA
<213> ORGANISM: Artificial Sequence
<220> FEATURE:
<223> OTHER INFORMATION: Synthesized repair oligonucleotide
<220> FEATURE:
<221> NAME/KEY: misc_feature
<222> LOCATION: (26)..(30)
<223> OTHER INFORMATION: n is A, C, T or G, where the specific groups of
      bases from positions 26 to 30 are listed in Table 3
```

-continued

```
<400> SEQUENCE: 62
tgcaggacca gagaattcga atacannnnn tcctactgag                    40
```